United States Patent [19]

Smith et al.

[11] Patent Number: 5,624,398

[45] Date of Patent: Apr. 29, 1997

[54] ENDOSCOPIC ROBOTIC SURGICAL TOOLS AND METHODS

[75] Inventors: Kevin W. Smith, Coral Gables; Juergen A. Kortenbach, Miami Springs; Charles R. Slater; Anthony I. Mazzeo, both of Fort Lauderdale; Theodore C. Slack, Jr., Miami; Thomas O. Bales, Coral Gables, all of Fla.

[73] Assignee: Symbiosis Corporation, Miami, Fla.

[21] Appl. No.: 597,423

[22] Filed: Feb. 8, 1996

[51] Int. Cl.$^6$ .......................... A61M 37/00; B25J 15/02
[52] U.S. Cl. .................................. 604/95; 901/35
[58] Field of Search ..................... 604/95, 97; 901/31, 901/39

[56] References Cited

U.S. PATENT DOCUMENTS

| | | | |
|---|---|---|---|
| 4,705,038 | 11/1987 | Sjostrom et al. | 128/305 |
| 4,880,015 | 11/1989 | Nierman | 128/751 |
| 5,059,203 | 10/1991 | Husted | 606/159 |
| 5,174,300 | 12/1992 | Bales et al. | 128/751 |
| 5,209,747 | 5/1993 | Knoepfler | 606/16 |
| 5,312,391 | 5/1994 | Wilk | 606/1 |
| 5,330,502 | 7/1994 | Hassler et al. | 606/205 |
| 5,431,645 | 7/1995 | Smith et al. | 606/1 |

Primary Examiner—Michael Powell Buiz
Assistant Examiner—Nancy Connolly Mulcare
Attorney, Agent, or Firm—David P. Gordon

[57] ABSTRACT

The methods and devices of the invention include an encoder, an endoscopic robotic instrument, and an encoder/robotic instrument interface. A preferred embodiment of the encoder has a chest/shoulder plate provided with telescoping tubes and joints. Each joint is provided with a direct drive potentiometer to monitor movement and provide a corresponding signal. The chest plate is preferably adaptable to a large range of human chest sizes and the telescopic segments are strapped to the arms of the practitioner at the elbows. A pistol grip is provided at the wrist end of the telescopic segments. According to the presently preferred embodiment, the encoder encodes flexion and rotation at the shoulder, elbow and wrist of each arm in addition to gripping at each hand. The encoding device is coupled to a circuit which operates a servo system. The servo system includes a series of servo motors. A series of pulleys corresponding to the number of servo motors are arranged in a housing. The robotic instrument preferably comprises two arms mounted at the distal end of a multi-lumen tube. Each arm has rotational and flexional joints corresponding to the shoulder, elbow, and wrist of the practitioner. Tendons are coupled to the pulleys of the servo motors and are fed through the multi-lumen tube to the joints of the two arms.

15 Claims, 15 Drawing Sheets

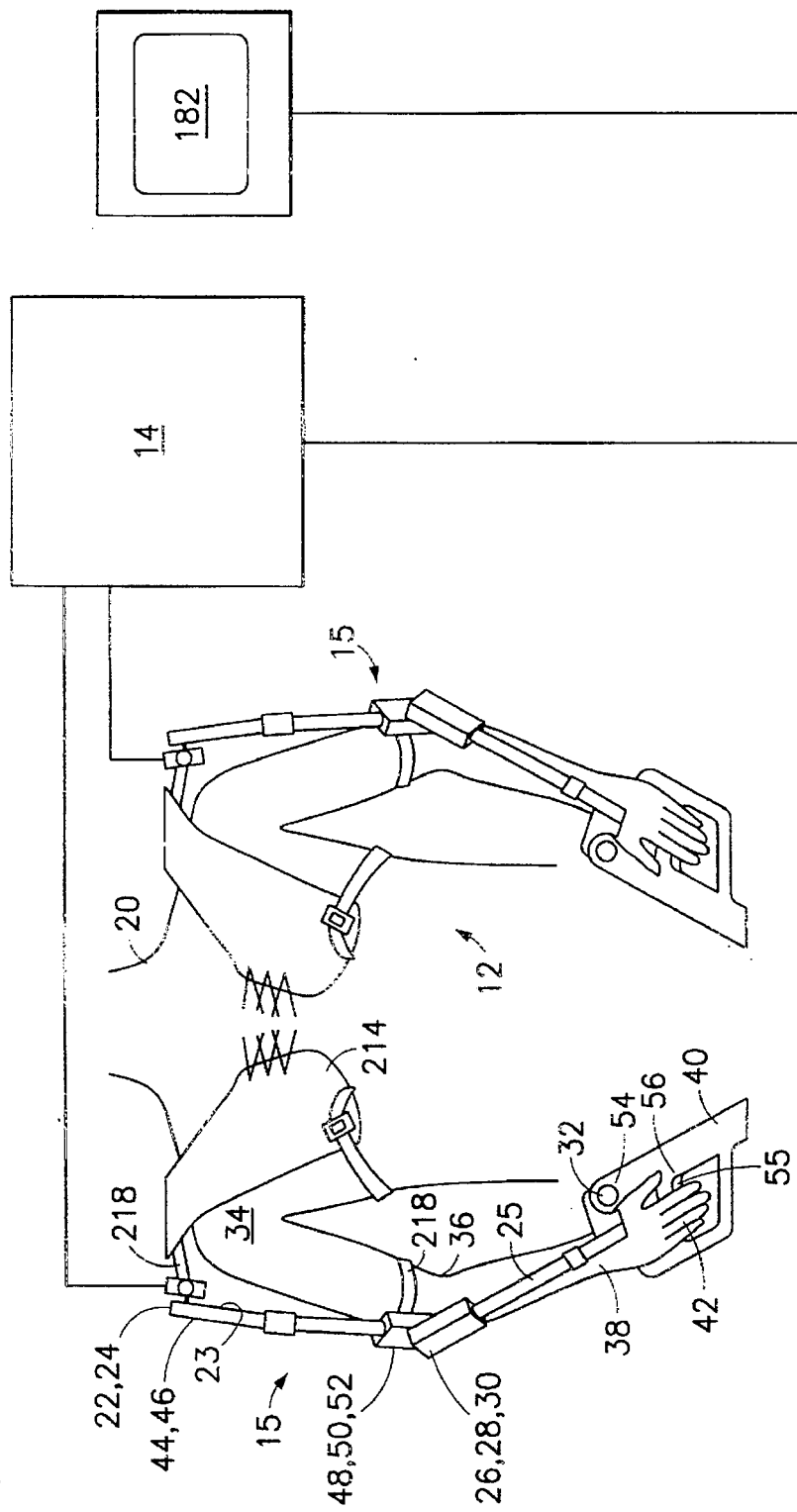

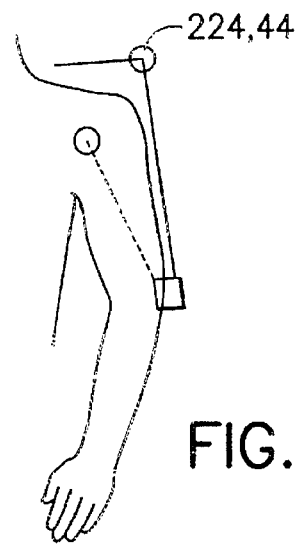
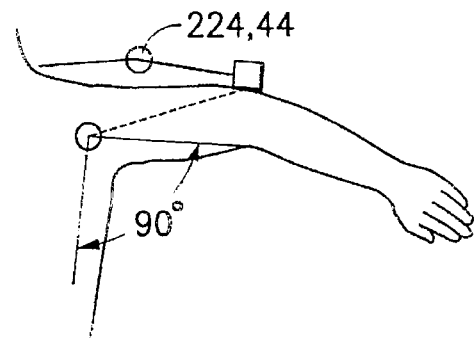
FIG. 7      FIG. 8
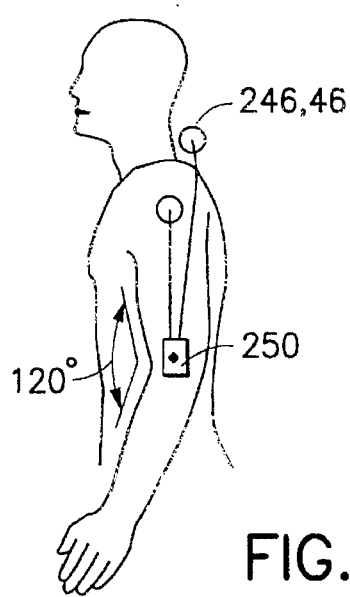
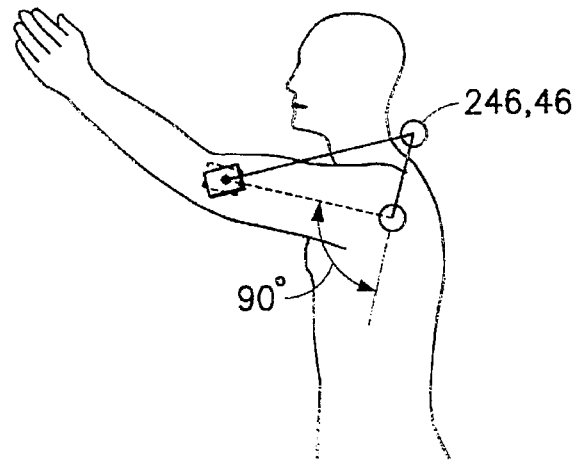
FIG. 9      FIG. 10
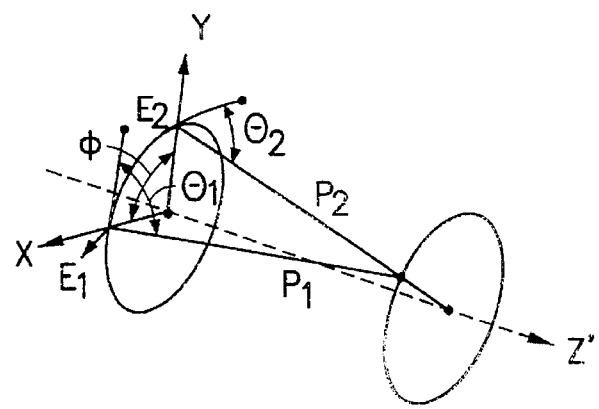
FIG. 11

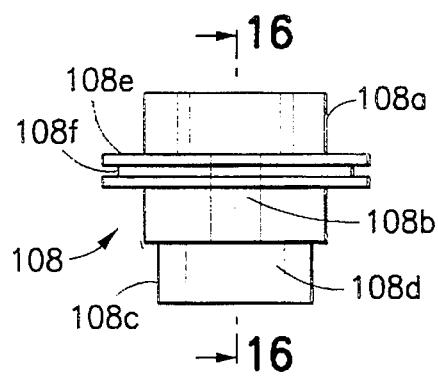
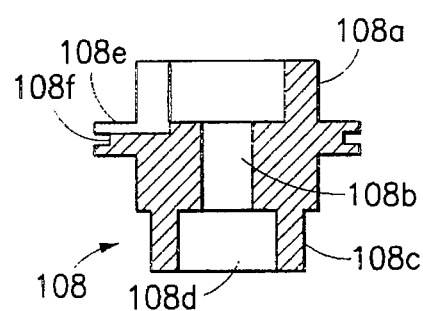
FIG. 15  FIG. 16
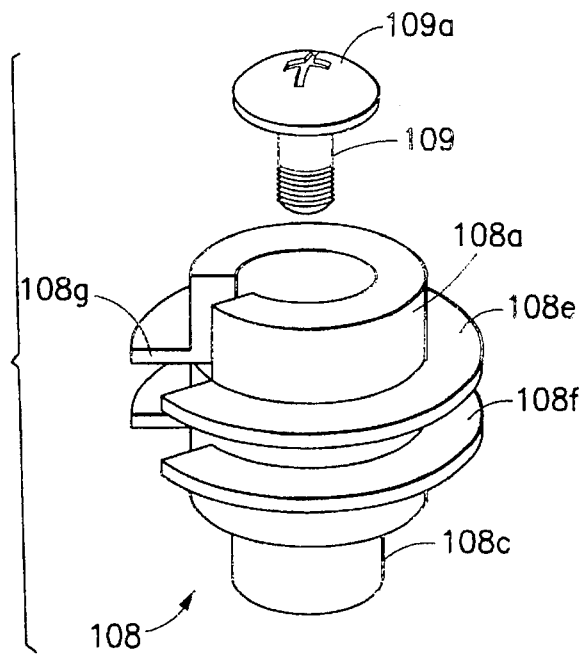
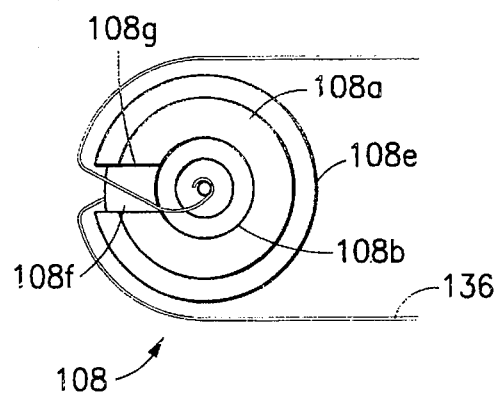
FIG. 17  FIG. 18
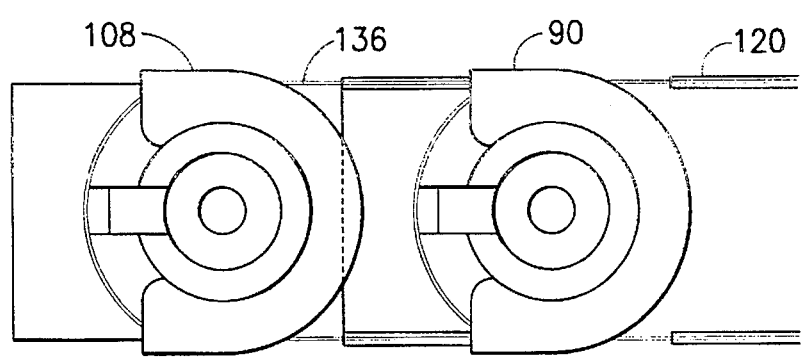
FIG. 19

ENDOSCOPIC ROBOTIC SURGICAL TOOLS AND METHODS

BACKGROUND OF THE INVENTION

A. Field of the Invention

The invention relates to endoscopic surgical tools and methods. More particularly, the invention relates to endoscopic methods and devices having robotic capabilities.

B. State of the Art

Endoscopic surgery is widely practiced throughout the world today and its acceptance is growing rapidly. In general, endoscopic surgery involves one or more incisions made by trocars where trocar tubes are left in place so that endoscopic surgical tools may be inserted through the tubes. A camera or magnifying lens is often inserted through one trocar tube, while a cutter, dissector, or other surgical instrument is inserted through another trocar tub for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut with another surgical instrument; all under view of the surgeon via the camera.

By 1996, it is expected that more than two million additional endosurgeries will be performed per year that, in 1990, were done via open surgery (MedPRO Month, I:12, p.178). The advantages of endoscopic surgery are clear in that it is less invasive, less traumatic and recovery is typically quicker. As a result, many new tools and devices for use in endosurgery are introduced every year. For example, it is now known how to use a powered microsurgical tool for intravascular surgery such as that disclosed in U.S. Pat. No. 5,059,203 to Husted. Husted teaches a miniature rotatable work wheel having a cutting blade that is integrally formed with a drive hub and axle and mounted for rotation at the end of a casing member. The casing member is a multi-lumen tube. A single monofilament drive line is looped around the drive hub and extends through separate lumens of the multi-lumen tube to a source of drive power. The drive hub also has a cupped cross section for inhibiting the monofilament drive line from riding off the hub. A drag load is applied to the payout end of the monofilament drive line close to the drive hub. The rotating wheel may be a cutting wheel or an abrading wheel, and is used primarily for opening occluded blood vessels. Endoscopic surgical tools with articulate end effectors are also now known. U.S. Pat. No. 4,880,015 to Nierman discloses a biopsy forceps for use in a flexible fiberoptic bronchoscope. Nierman's forceps are provided with an increased range of operability when obtaining tissue samples due to a hinge joint located between the forceps grippers and the cable from which the grippers extend.

Meanwhile, the art of robotics is also developing rapidly. While originally conceived of in fiction, modern robotics involves discrete specialized applications often in the area of manufacturing, but also in the areas of research and development and where hazardous environments must be traversed. In this latter application, robotics often involves electro-mechanically activated articulate members emulating human arms and hands which are operated by an encoding device responsive to the articulation of human arms and hands of an practitioner. Known encoding devices generally include an exoskeleton or sleeve which fits over the human arm of the practitioner. The encoding sleeve is provided with joints corresponding to the joints in a human arm and one or more ring bearings all of which translate motion by the human arm of the practitioner into mechanical, electrical, or electro-mechanical signals. These signals generated by the encoder are then transmitted to a robotic arm which responds to the signals from the encoder. The robotic arm is usually moved by servo motors which are located in the robotic arm joints. The object of this type of arrangement is to provide a mechanical or electro-mechanical arm which will mimic the movements of the human arm of an practitioner. Robotic arms are also usually provided with some type of gripper which is activated by hand movement of the practitioner. These types of robotic arm arrangements are most often used in hazardous environments such as the handling of nuclear materials, the disarming of bombs, and in space exploration (where the signals from the encoder to the robotic arm are transmitted over long distance by radio waves).

Early robotic arms were clumsy and useful only for completing gross tasks such as lifting, pouring, twisting and the like. It was difficult to obtain an arrangement of encoder and robot arm which had the responsiveness of a human arm. This difficulty stemmed from the quality of the servo motors, the difficulty in encoding the articulations of the human arm, and the lack of feedback to the encoder. State of the art robotic arms, however, have overcome many of the difficulties encountered by the early robotic arms. It is now possible to construct robotic arms which have a wide range of movements closely mimicking the articulations of the human arm and which provide feedback to the encoder to more correctly mimic the movements of the practitioner. State of the art robotic arms are capable of performing sophisticated tasks such as welding, soldering, sewing, manipulation of a variety of tools, handling of small pieces, etc. Encoders are now commonly provided with feedback mechanisms which offer the practitioner varying resistance corresponding to the resistance encountered by the robotic arm.

Recent developments in robotics and in telecommunications have created a new art called "virtual presence". In virtual presence, an encoder with audio, video, and tactile feedback is worn by a human "participant" and is connected through a transceiver to a robotic apparatus having audio, video and tactile sensors at a distant location. The object of virtual presence is to allow the human participant to act and feel as if the participant is actually present at the distant location. Virtual presence technology has been applied in the aerospace industry for controlling remote space probes, in oceanography for controlling deep sea probes, and in environmental sciences for the handling of hazardous materials.

While endoscopic surgery is ever gaining in acceptance, it is still often more difficult to perform than open surgery insofar as the surgeon must view the surgical site through an endoscope or a camera rather than viewing it directly through a large incision. In this sense, endosurgery using video cameras is similar to virtual presence since the participant (in this case the surgeon) does not see the surgical site directly, but rather sees a virtual representation of the surgical site on a television screen. However, while virtual presence virtually places the participant in a distant scene, in endosurgery, the surgeon must reach into the televised scene using tools which function unlike human arms and hands. In state of the art endosurgery the surgeon is limited to tasks for which tools are available, while in open surgery the surgeon can still apply the wide range of articulation available to human arms and hands. Nevertheless, in either type of surgery, the surgeon must be within arm's length of the patient.

Despite advances in robotics, the robotic techniques have heretofore never been used in endoscopic surgical instruments or procedures, probably because the robotic instruments are relatively large and the endoscopic instruments are relatively tiny.

SUMMARY OF THE INVENTION

It is therefore an object of the invention to provide an endoscopic tool having a plurality of rotational and flexional joints.

It is also an object of the invention to provide an endoscopic tool having a pair of articulate robotic arms.

It is another object of the invention to provide robotic endosurgical tools which are small enough to extend through trocar tubes but which provide a surgeon with substantially all of the articulation available in open surgery.

It is also an object of the invention to provide an endoscopic tool having articulate robotic arms which are operable by servo motors.

It is another object of the invention to provide endoscopic robotic arms which are coupled to servo motors using tendons and pulleys.

It is also an object of the invention to provide endoscopic robotic arms which are flexional and rotational through the movement of tendons.

It is also an object of the invention to provide and endoscopic robotic arm with small diameter tendons which are durable and which are positively coupled to the arm.

It is still another object of the invention to provide robotic endoscopic instrument arms which closely mimic the movements of human arms.

It is another object of the invention to provide a robotic endoscopic instrument arm which is controlled by an encoder worn by a surgeon.

It is also an object of the invention to provide a robotic encoder for controlling an endoscopic tool which is adaptable to fit any size surgeon and which is easy to put on..

It is another object of the invention to provide feedback mechanisms in the robotic arms so that the arms are more responsive to movements registered by the encoder.

It is also an object of the invention to provide tactile feedback means in the robotic grippers so that the surgeon can tell the amount of force applied at the grippers.

It is yet another object of the invention to provide a coupling mechanism whereby robotic endoscopic instrument arms may be coupled to an encoder so that the instrument arms are disposable and the encoder is reusable.

It is also an object of the invention to provide a multilumen tube through which robotic endoscopic instrument arms and an endoscopic camera extend and through which supplies and the like are delivered to the surgical site for use by the robotic arms.

It is still another object of the invention to provide multidimensional viewing means and remotely coupled encoder means so that a surgeon may operate and view the operation from a location remote from the patient.

In accord with these objects which will be discussed in detail below, the methods and devices of the present invention include an encoder, an endoscopic robotic instrument, and an encoder/robotic instrument interface. A preferred embodiment of the encoder has a chest/shoulder plate provided with telescoping tubes and joints. Each joint is provided with a direct drive potentiometer to monitor movement and provide a corresponding signal. The chest plate is preferably adaptable to a large range of human chest sizes and the telescopic segments are strapped to the arms of the practitioner at the elbows. A pistol grip is provided at the wrist end of the telescopic segments. According to the presently preferred embodiment, the encoder encodes flexion and rotation at the shoulder, elbow and wrist of each arm in addition to gripping at each hand.

The encoding device is coupled to a circuit which operates a servo system. The servo system includes a series of servo motors to move to positions correlating to the potentiometer positions which correspond to the position of the arm of the practitioner wearing the encoder. The servo motors are mounted in an interface housing with the rotational axes of their shafts parallel. The rotational shaft of each servo motor is provided with a quick connecting end. A series of pulleys corresponding to the number of servo motors are arranged in a single tray-like housing. Each pulley is provided with a self-aligning socket designed to mate with a corresponding servo motor shaft. All of the pulleys are mounted on all of the shafts simultaneously and quickly by coupling the tray-like housing to the servo motor housing and are similarly quickly disconnectable from the servo motors. According to the presently preferred embodiment, for each arm, seven servo motors and corresponding pulleys are provided for responding to flexion and rotation at the shoulder, elbow and wrist of each arm in addition to gripping at each hand. Fourteen servo motors and corresponding pulleys are provided for a pair of arms and hands.

The robotic instrument preferably comprises two arms mounted at the distal end of a multi-lumen tube. Each arm has rotational and flexional joints corresponding to the shoulder, elbow, and wrist of the practitioner. Tendons are coupled to the pulleys of the servo motors and are fed through the multi-lumen tube to the joints of the two arms. The endoscopic robotic arms preferably mimic human arms having movements for shoulder rotation, shoulder flexion, upper arm rotation, elbow flexion, lower arm rotation and wrist flexion. In addition, grippers are mounted at the distal end of the robotic arms to provide a limited hand movement.

Preferred aspects of the encoder include its adjustability to fit different size users, its light weight, and the placement of potentiometers to compensate for differences in the movement of the exoskeleton relative to the movement of the user's arm. The potentiometers are preferably supplied with op-amp followers and are opto-isolated from the control circuit.

Preferred aspects of the control circuit include its adjustability to the arm movements of different users and the adjustability of the relative movement of each robot arm joint relative to the encoded movements of the user's arm joints. The presently preferred control circuit includes, for each potentiometer in the encoder, a pair of adjustable voltage regulators and a pulse generator formed from an astable and a monostable timer. The voltage regulators supply an upper and a lower voltage to the potentiometer and the potentiometer selects a voltage between the upper and lower voltage and supplies that voltage to the pulse generator. The pulse generator generates a pulse train in which the length of the pulses is proportional to the voltage selected by the potentiometer. The upper and lower voltages for each potentiometer are independently adjustable and determine the range of movement of the corresponding robot arm joint relative to movement of the encoder joint.

Preferred aspects of the servo system include providing the servo motors with self-aligning splined shafts and axially offsetting some of the pulleys in the pulley tray relative to other pulleys so that the tendons may be easily threaded through the pulley tray. Each pulley preferably includes a radial slot and an axial screw. A tendon is attached to a pulley by threading its ends through the radial slot and around the axial screw. Tightening the axial screw secures the tendon to the pulley. The pulley tray is preferably provided with ramped parts which deflect the tendons upward for easier assembly of the tray.

The robotic arms preferably include alternating rotational and flexional joints. Each flexional joint preferably includes a clevis having a cylindrical stem and each rotational joint preferably includes a socket in which a corresponding clevis stem is rotationally mounted. Each socket distal of the most proximal socket has a stem which is mounted between arms of a respective clevis. The most proximal rotational joint is preferably directly driven and the remainder of the rotational joints are preferably pulley driven. The flexional joints are preferably pulley driven. The preferred pulley driven rotational joint includes a two layered pulley mounted on a socket with its axis of rotation perpendicular to the longitudinal axis of the socket. The clevis stems preferably include stepped twist drums. The tendon for a rotational joint wraps approximately ninety degrees around a first layer of the layered pulley, approximately half way around a first step of the twist drum, approximately half way around a second step of the twist drum, and approximately ninety degrees around a second layer of the layered pulley. An axial bore between the first step and the second step of the twist drum facilitates location of the tendon and secures the tendon against slippage. The preferred pulley driven flexional joints include a pulley which is mounted on a socket stem which is mounted between arms of a clevis. The tendon for a flexional joint wraps approximately ninety degrees around the top of the pulley, wraps around the socket stem and wraps approximately ninety degrees around the bottom of the pulley. A screw in the clevis stem secures the tendon to the clevis stem and prevents slippage.

The tendons are preferably encased by individual coiled sheaths and are threaded around the robot arms so as to avoid interference with each other and with movement of the robot arms. Each pair of grippers is preferably spring biased in the open position and is operable by a single pull wire in a protective coil sheath.

Additional objects and advantages of the invention will become apparent to those skilled in the art upon reference to the detailed description taken in conjunction with the provided figures.

BRIEF DESCRIPTION OF THE DRAWING

FIGS. 6 through 11 are schematic diagrams showing axes of upper arm movement;

FIG. 15 is a transparent side elevation view of a single pulley of the pulley tray of FIG. 13;

FIG. 16 is a cross sectional view along line 16—16 of FIG. 15;

FIG. 17 is an exploded perspective view of a pulley and a tendon coupling screw;

FIG. 18 is a top view of a pulley and a tendon;

FIG. 19 is a top view of two pulleys and tendons;

DETAILED DESCRIPTION OF THE PREFERRED EMBODIMENTS

A. Overview

Figure 1B:
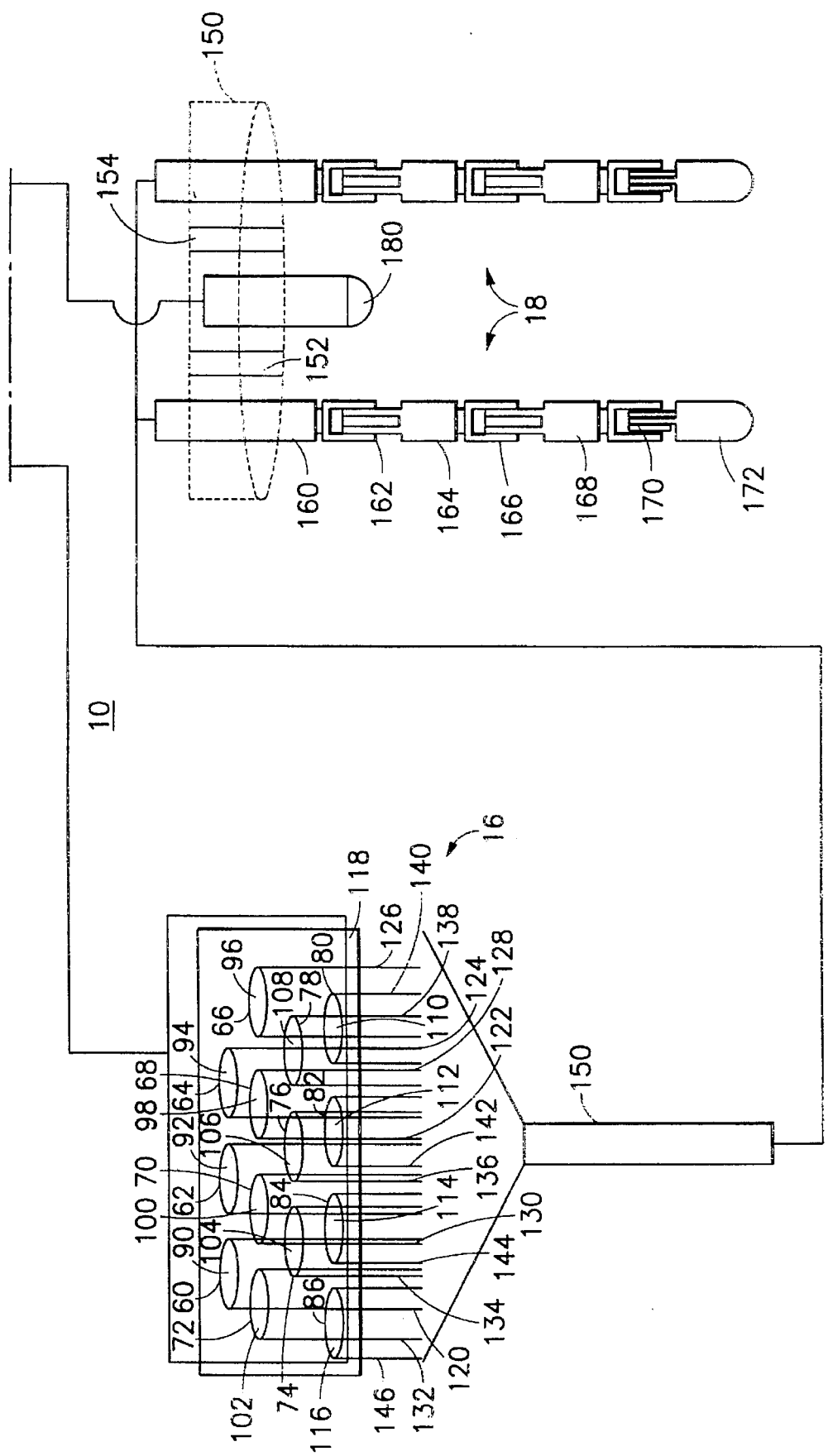
FIG. 1 is a schematic illustration of one embodiment of an endoscopic robotic surgical tool according to the invention.

Turning now to FIG. 1, a first embodiment of an endoscopic robotic tool 10 according to the invention generally includes an exoskeleton encoder 12, a control circuit 14, a servo system 16, and a pair of remote robot arms 18. The exoskeleton encoder 12 fits over the shoulders and chest, and attaches to the arms of a practitioner 20. Rotational and flexional joints 22, 24, 26, 28, 30, 32 are provided on the encoder 12 for each shoulder 34, elbow 36 and wrist 38 of the practitioner, while a pistol grip 40 is provided for each of the hands 42 of the practitioner. In total, seven transducers 44, 46, 48, 50, 52, 54, 56 are provided in each arm of the encoder to register rotational and flexional movements of the shoulders 34, elbows 36, and wrists 38 as well as gripping movement of the hands 42 of the practitioner. The transducers are all coupled to a control circuit 14 which in turn provides outputs to an array of fourteen servo motors 60, 62, 64, 66, 68, 70, 72, 74, 76, 78, 80, 82, 84, 86. The servo motors are coupled respectively to pulleys 90, 92, 94, 96, 98, 100, 102, 104, 106, 108, 110, 112, 114, 116 which in turn are coupled to tendon loops 120, 122, 124, 126, 128, 130, 132, 134, 136, 138, 140, 142, 144, 146, i.e., one tendon loop per motor. The tendons are fed through a multi-lumen tube 150 to the remote robot arms 18 which are mounted at the distal end of the tube 150.

Each robot arm is provided with three rotational joints 160, 164, 168 and three flexional joints 162, 166, 170, and the distal end of each robot arm is provided with a gripper 172. Thus, the fourteen tendon loops 120, 122, 124, 126, 128, 130, 132, 134, 136, 138, 140, 142, 144, 146, are each coupled to a respective one of the seven joints and the gripper on each arm. However, as discussed in more detail below, the shoulder rotational joint 160 may be controlled by a torsion tube rather than a tendon loop, and the gripper 172 may be controlled by a tendon pull-wire rather than a tendon loop. Moreover, while each tendon is preferably encased in a coil sheath, the shoulder flexional joint may be controlled by a tendon which is not sheathed since the path taken by the tendon is a relatively straight line through the multilumen tube and the tendon does not bend through a path as the other joints are flexed.

The distal end of the multi-lumen tube 150 is also provided with a camera lens 180 which is optically coupled to a video camera (not shown). Output from the video camera is transmitted by either wired or wireless communications to a monitor 182 viewable by the practitioner 20. Additional lumens 152, 154 are preferably provided in the multi-lumen tube 150 for the delivery of supplies to the surgical site, and/or for suction, irrigation, and the like. The pulleys 90, 92, 94, 96, 98, 100, 102, 104, 106, 108, 110, 112, 114, 116 are preferably arranged in a tray 118 which is detachable from the array of servo motors 60, 62, 64, 66, 68, 70, 72, 74, 76, 78, 80, 82, 84, 86. The outputs from the control circuit 14 may be transmitted to the array of servo motors 60, 62, 64, 66, 68, 70, 72, 74, 76, 78, 80, 82, 84, 86 by wired or wireless communications and the distance between the control circuit and the servo motors may be several feet or several thousand miles. The distance between the encoder 12 and the control circuit 14 is preferably only several feet and the length of the multi-lumen tube 150 is also preferably only several feet. The outer diameter of the multi-lumen tube 150 is small enough to fit through a trocar tube (not shown) and the grippers 172 on the robot arms 18 are similar in size to the grippers of known endoscopic instruments.

As will be discussed in detail below, the encoder may include more or fewer transducers, and the transducers may take any of many forms such as potentiometers, photoelectric sensors, Hall effect sensors, inertial devices, or sonic sensors. The pistol grips may include controls for suction, irrigation, and/or cautery. The exoskeleton of the encoder may take different forms, as well. For example, positions of the practitioner's arms could be detected by sonar, IR or visible laser scanning, in which case, the exoskeleton could be replaced by a series of reflectors attached to the practitioner's arms. In order to ease fatigue, the practitioner's arms could be suspended and the suspension assembly used to encode arm movement.

Those skilled in the art will appreciate that the configuration of the control circuit will depend to a greater or lesser degree on the configuration of the encoder and the type of servo system used. In this regard, it will be understood that the servo system need not utilize rotary motors with pulleys and cables, but may use other drive means such as motorized jack screws, hydraulic, or pneumatic drive means. The coupling of the robot arms to the servo system will also depend on what type of drive means is used.

The robot arms may be controlled in part with a direct drive in lieu of tendons and pulleys. The path of the tendons from the robot arms to the servo system may be varied according to other considerations which will be understood from the discussion below. Hydraulics or pneumatics may be used to control the robot arms instead of tendons and pulleys. The grippers at the ends of the robot arms may be cutters or other types of end effectors and the robot arms may be provided with removable, replaceable end effectors. In one embodiment, the robot arms are retractable into the multi-lumen tube and the tube is provided with means for the practitioner or an on-site nurse or assistant to change end effectors during the course of a procedure.

It is also preferable to provide various types of feedback in the system. Generally, visual feedback to the practitioner will always be provided, but such visual feedback may be configured in various ways. Using the proper optics, stereoscopic visual feedback can be provided. Some practitioners may find it useful to have the video image transposed horizontally so that the sensory impression is that of looking into a mirror. It is also possible to provide visual feedback from infrared, ultrasound or other sensors located appropriately relative to the surgical site. Tactile feedback is desirable at least in the trigger portions of the encoder so that the practitioner can judge how much force is applied by the grippers. Other sensory feedback to the practitioner is also possible with the appropriate transducers. Positional feedback from the robot arms to the control circuit is desirable in most instances. For example, when tendons are capable of kinking, stretching, or slipping, it is advisable that the control circuit determine whether the signal to the servo system has indeed effected the desired movement of the robot arm. Various means for providing these kinds of feedback are discussed in detail below.

The basic operation of the endoscopic robotic tool, shown in FIG. 1, is as follows. The practitioner 20 who is to perform an endoscopic procedure dons the exoskeleton encoder 12 and turns on the video monitor 182. An assistant (not shown), who is in communication with the practitioner 20, incises the patient (not shown) with a trocar (not shown). The assistant couples the pulley tray 118 to the array of servo motors 60, 62, 64, 66, 68, 70, 72, 74, 76, 78, 80, 82, 84, 86 and inserts the distal end of the multi-lumen tube 150 through a trocar tube (not shown) and locates the robot arms 18 in the vicinity of the surgical site. The tray of servo motors 16 is located a convenient distance from the surgical site with the flexible sheathed tendons extending to the multilumen tube which holds the robot arms. The servo motor tray may be supported by an adjustable clamping means connected to the operating table or other support. The practitioner 20 may direct the assistant to relocate the robot arms 18 according to information provided via the video monitor 182. When the control circuit 14 is activated, movement of the practitioner's arms 34, 36, 38 is replicated in the robot arms 18. When the practitioner grips one of the pistol grips 40, the gripper 172 on a corresponding robot arm 18 is closed. Thus, the tool 10 provides the practitioner 20 with a virtual presence of two arms and hands and vision at the surgical site.

From the foregoing, those skilled in the art will appreciate that a practitioner wearing the encoder and viewing the video monitor is equipped to perform an endoscopic procedure at a location remote from the surgical site. The encoder, control circuit and video monitor may be located many thousands of miles from the surgical site and coupled to the servo motors and video camera by any telecommunications device such as a wireless transceiver or a telephone modem. As mentioned above, however, there must be an assistant near the surgical site initially to locate the robot arms according to instructions from the practitioner. Those skilled in the art will appreciate that the assistant is preferably provided with a simultaneous video display for locating the robot arms. Hands free audio-visual communication means is preferably provided between the practitioner and the assistant. It will also be appreciated that the assistant will be called upon during the course of the endoscopic procedure to relocate the robot arms and to supply materials through a lumen in the multi-lumen tube or through an additional trocar tube to the surgical site for use by the robot arms.

The following discussion deals with each major component of the endoscopic robotic tool and explains in detail the various embodiments of each component. In addition, the use of remote communications systems with the endoscopic robotic tool is discussed in detail. Methods of operating the endoscopic robotic tool are addressed and yet additional alternate embodiments of the tool are disclosed.

B. The Encoder

1. Exoskeleton a. Electromechanical Using Potentiometers

Figure 2:
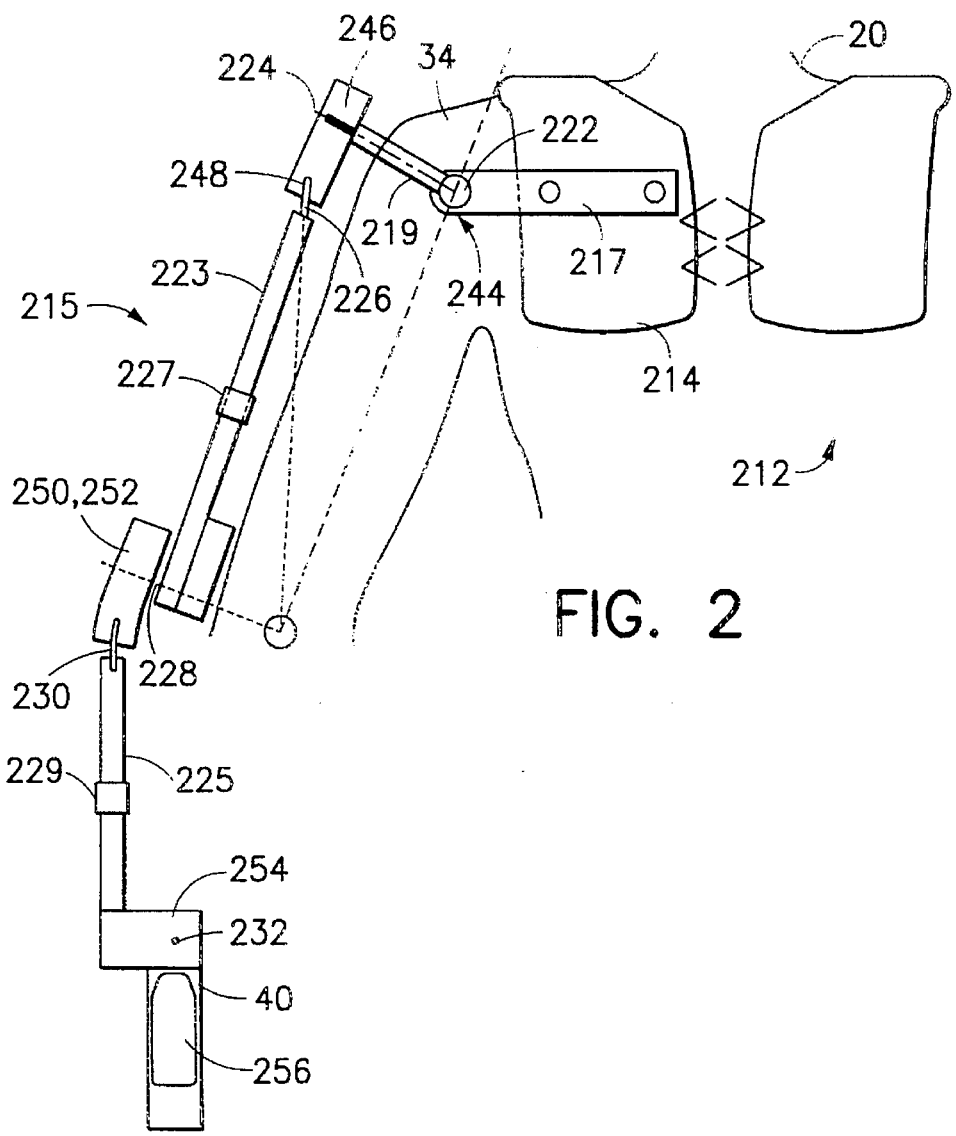
FIG. 2 is a rear view of the left portion of an exoskeleton encoder.
Figure 3:
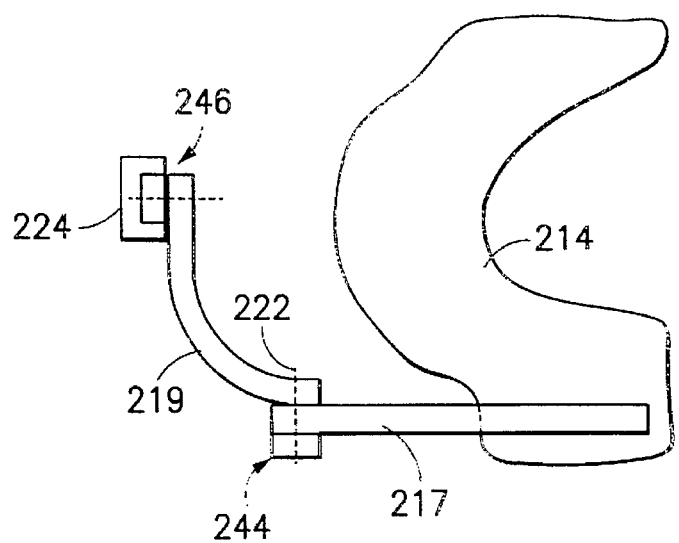
FIG. 3 is a top view of the left portion of the encoder of FIG. 2.

Turning now to FIGS. 1 through 3, two preferred embodiments of an encoder 12, 212 each include a pair of chest/shoulder plates 214 and a respective pair of articulating arms 15, 215, each of which terminates with a pistol grip 40. It will be appreciated that each chest/shoulder plate and articulating arm assembly is a mirror image of the other. The following discussion of one chest/shoulder plate and articulating arm, therefore applies to each of them. The chest/shoulder plate 214 is adaptable to fit a variety of chest sizes and the articulating arms 15, 215 are adjustable in length. The encoder designs described herein are adjustable to fit virtually any practitioner weighing between 100 and 300 pounds and having an arm length (neck to wrist) between twenty-four and thirty-six inches. The chest/shoulder plate 214 extends over the shoulders of the practitioner and is strapped or laced across the chest, across the back and under the armpits as seen best in FIG. 1. The articulating arms 15, 215 are attached to respective arms of the practitioner by straps 218 located just above the elbow 36. The hands 42 of the practitioner fit into the pistol grips 40.

A first preferred embodiment of the encoder 212 is shown in FIGS. 2 through 5. Starting at the left shoulder plate 214, a horizontal member 217 extends outward from the rear of the shoulder plate 214 and terminates at a point behind the shoulder 34 of the practitioner. A ninety degree curved member 219 is rotationally attached to the end of the horizontal member 217 at rotation point 222 and a shoulder rotation transducer 244 is coupled to the horizontal and curved members. A telescoping upper arm member 223 is rotationally coupled to the curved member 219 at rotation points 224 and 226 so that it is rotatable about two orthogonal axes relative to the curved member 219. A shoulder flexion transducer 246 and an upper arm rotation transducer 248 are coupled to the upper arm member 223 and the curved member 219. A telescoping lower arm member 225 is rotationally coupled to the lower end of the upper arm member 223 at rotation points 228 and 230 so that it is rotatable about two orthogonal axes relative to the upper arm member 223. An elbow flexion transducer 250 and a wrist rotation transducer 252 are coupled to the upper and lower arm members 223, 225 at the elbow. A spring-biased pistol grip 40 is rotationally coupled at rotation point 232 to the lower end of the lower arm member 225 and a wrist flexion transducer 254 is coupled to the lower arm member 225 and the pistol grip 40. A grip transducer 256 is coupled to the trigger 255 in the pistol grip 40. Each of the telescoping arm members 223, 225 is provided with a locking collar 227, 229 so that the length of the arm members may be adjusted and locked.

In sum, each arm, therefore, is provided with seven transducers 244, 246, 248, 250, 252, 254, 256. The transducers are preferably potentiometers which are directly coupled to the members described above. Six of the potentiometers 244, 246, 248, 250, 252, 254 register changes in the position of the arms of the practitioner and the seventh potentiometer 256 registers the grip of the practitioner.

Returning to FIG. 1, a slightly different second preferred embodiment of the encoder is shown. Starting at the shoulder plate 214, a horizontal member 218 extends outward from on top of the shoulder plate 214 and terminates at a point above the shoulder of the practitioner. A freely telescoping upper arm member 23 is rotationally coupled to the horizontal member 218 at rotation points 22, 24 so that it is rotatable about two orthogonal axes relative to the horizontal member 218. A shoulder rotation transducer 44 and a shoulder flexion transducer 46 are coupled to the upper arm member 23 and the horizontal member 218. A telescoping lower arm member 25 is rotationally coupled to the lower end of the upper arm 23 member at rotation points 26, 28 so that it is rotatable about two orthogonal axes relative to the upper arm member 23. An upper arm rotation transducer 48, an elbow flexion transducer 50 and a wrist rotation transducer 52 are coupled to the upper and lower arm members at the elbow. The remainder of the encoder of FIG. 1 is the same as the encoder of FIGS. 2 through 5.

Figure 6:
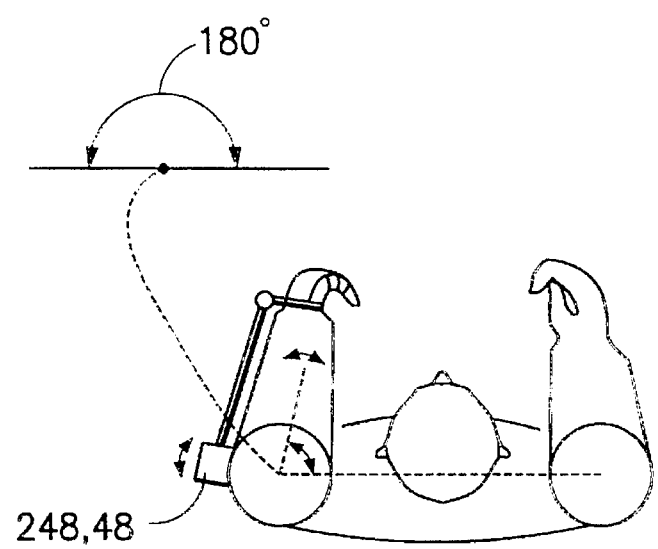

FIGS. 6 through 12 illustrate the range of upper arm movements registered by the encoder. The first potentiometer 244 mentioned above registers "shoulder rotation" which is defined as the movement of the arm in a first vertical plane which touches both shoulders. The preferred range of shoulder rotation is shown in FIGS. 7 and 8 and is approximately 90°. The second potentiometer 46, 246 registers "shoulder flexion" which is movement of the arm through a second vertical plane which is perpendicular to the first vertical plane and which touches only the one shoulder being flexed. FIGS. 9 and 10 show the preferred range of shoulder flexion which is also approximately 90°. The third potentiometer 48, 248 mentioned above registers "upper arm rotation" which is illustrated in FIGS. 6 and 11 and is preferably approximately 180°. The fourth potentiometer 50, 250 mentioned above registers "elbow flexion" which preferably has a range of approximately 120° as indicated in FIG. 9.

FIGS. 7 through 10 also illustrate that the shoulder rotation and flexion transducers in the encoder of FIG. 1 provide a slightly inaccurate registration of the arm movements of the practitioner. For example, as seen by comparing FIGS. 7 and 8, the center of rotation of the shoulder transducers is offset from the center of rotation of the practitioner's shoulder and because of this, the transducers do not register the exact amount of arm movement. Likewise, a comparison of FIGS. 9 and 10 show that a flexional upper arm movement of 90° will register as less than 90° by the transducer 46, 246. Nevertheless, the encoder of FIG. 1 is more adaptable to different sized practitioners and the slight loss in accuracy of the encoder is negligible and can be corrected electronically if desired.

The encoder of FIG. 1 has additional advantages in that it is more comfortable and less restrictive for the practitioner than the encoder of FIG. 2. In particular, the potentiometers for registering "shoulder flex" and "shoulder rotation" can be mounted together in one small box above the practitioner's shoulder as shown in FIG. 1. This helps make the encoder a "one size fits all" system. Any "throw" differences from one practitioner to another can be compensated for by electronic adjustment. Twist motions will result in some extraneous input to other adjacent encoders. For example, a wrist twist results in some elbow flex motion. Upper arm twist results in some shoulder flex and rotation, etc. The amount of accuracy sacrificed by this encoder system is rapidly compensated for by the practitioner's brain. As will be discussed in detail below, it will also be noticed that the position of these transducers above the shoulder requires that the upper arm member telescope. The elbow is moved closer to the transducers when the arm is rotated from the position in FIG. 7 to the position in FIG. 8 and when the arm is flexed from the position in FIGS. 9 to the position in FIG. 10. The freely telescoping upper arm member compensates for this.

The registration of upper arm rotation is registered by a potentiometer 48, 248 mounted along side the elbow as seen in FIG. 1 or by a potentiometer mounted alongside the shoulder as seen in FIG. 2. In both embodiments, the potentiometer is slightly offset from the true axis of upper arm rotation as seen best in FIG. 6. This results in a small inaccuracy in registration of the upper arm rotation as seen in FIG. 11. As the upper arm rotates from P1 to P2 through an angle $\phi$, the elbow follows an arc path from point E1 to point E2. The angle between the upper and lower arm members increases from $\theta_1$ to $\theta_2$. This error is slight, and is compensated for by the practitioner. The result is that the robot follows the motion of the encoder, which is a close approximation.

Figure 4:
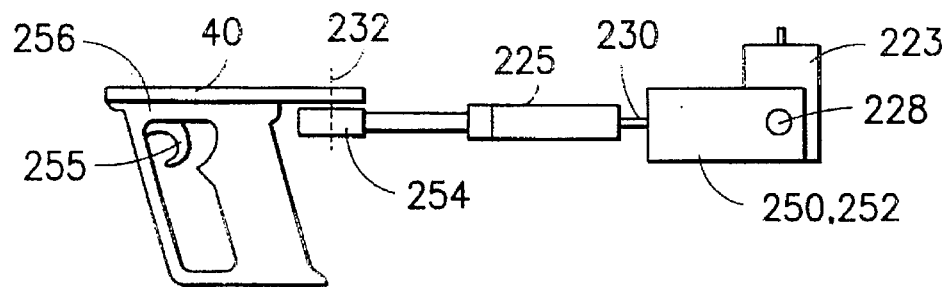
FIG. 4 is a broken side elevation view of the left lower arm portion of the encoder of FIG. 2.
Figure 5:
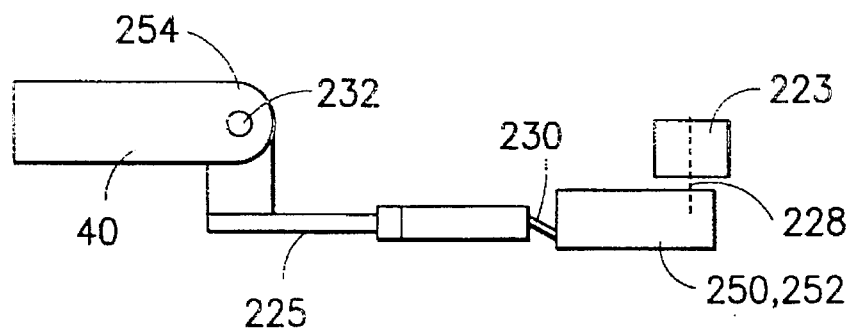
FIG. 5 is a broken top view of the left lower arm portion of the encoder shown in FIG. 4.

Both the elbow and the wrist flexion potentiometers are directly in line axially with the biological joints of the practitioner as seen in FIGS. 1, 4, and 5. In order to encode any twisting action in the forearm without adding excessive movements to either flex joint, the distance between the elbow potentiometers and the wrist potentiometer must not change when the arm is flexed. This is accomplished by making the length of the telescopic lower arm member lockable once its length is adjusted to fit the practitioner. The use of an L-shaped forearm connection to the pistol grip (seen best in FIGS. 2 and 5) allows the forearm rotation joint to register ±90° without interfering with the practitioner's arm movements. This geometry also minimizes disturbance of the elbow flex joint when rotating the forearm about a stationary axis.

The trigger 255 in the pistol grip 40 is preferably coupled to a solenoid which provides tactile feedback to the practitioner. The solenoid receives a signal based on the current drain in the servo motor which closes the gripper, e.g. 172 (FIG. 1). As the gripper encounters resistance and more force is applied by the servo motor, the current drain across the servo motor increases. The solenoid is arranged to provide a variable resisting force at the trigger which is proportional to the resistance encountered by the gripper.

While the encoder of FIG. 1 is the presently preferred embodiment, other types of encoders can be used. Since the encoder is reusable and separable from the remainder of the apparatus, a surgeon may prefer to use a more customized encoder. The preferred encoder takes advantage of direct drive potentiometers, but other encoders may use different means for registering the position of the arms of the practitioner.

b. Other Transducers

In lieu of potentiometers which are directly driven by the joints of the exoskeleton, the shafts of the potentiometers may be coupled to weights. As the exoskeleton moves the potentiometers relative to the earth, gravity holds the weight downward and the shaft of the potentiometer is thereby rotated. For example, a potentiometer having a base portion and a rotatable shaft portion is mounted by its base to an arm member of an exoskeleton at the rotational axis of the arm member. A vertically downward extending weight is attached to the shaft portion of the potentiometer. As the arm member is rotated about the rotational axis, the base of the potentiometer is also rotated. The weight on the shaft of the potentiometer remains vertically disposed, however, due to the action of gravity, and maintains the angular orientation of the shaft of the potentiometer constant. The base of the potentiometer is therefore rotated relative to the shaft of the potentiometer, which is equivalent to rotating the shaft of the potentiometer relative to the base of the potentiometer. The relative angular movement of the arm member is thereby encoded by the relative angular movement of the base of the potentiometer relative to the shaft of the potentiometer.

Another transducer using weights may be constructed from two concentric spheres with an interposed droplet of mercury or a freely moving weight. The relative position of the mercury droplet can be detected by capacitance, conductive strips, or by optical means. This type of transducer can detect position in multiple axes.

c. Photoelectric Transducers

A photoelectric transducer can be made from a rotatable disc having an optical gradient density surface and a peripheral weight. A photodetector aimed at the optical gradient density surface detects the angular position of the detector relative to the disc which is held stationary by the weight. The disc and the detector are mounted in a gimballed enclosure to keep the shaft of the disc horizontal.

2. Optical Without Exoskeleton

There are several possible embodiments of an encoder which does not require an exoskeleton. These embodiments of the encoder use optical sensors and an image processor to determine the movements of the arms of the practitioner and encode them for use by the servo system.

a. Laser Encoders

A first embodiment of an optical encoder without an exoskeleton includes a series of reflectors which are attached to the arms of the practitioner at the shoulder, elbow, wrist, and hand. At least two orthogonally disposed photodetectors are placed above and alongside the practitioner. A source of laser light is provided with a rotating mirror scanning device which directs the laser light at the reflectors and scans an area through which the reflectors are expected to move. As the arms of the practitioner move through space, the laser light detected by the photo-detectors varies. An image processor interprets the signals output from the photo-detectors and operates the servo motors to move the robotic arms.

3. Suspended Encoders

A suspended encoder according to the invention is similar to the electromechanical exoskeleton encoder described above. However, the arms of the practitioner are suspended in the air by cables which are attached to pulleys and dollies mounted in a frame above the practitioner. The pulleys and dollies are provided with transducers which detect their movement. As the arms of practitioner move, the cables translate this movement to movement of the pulleys and dollies and the transducers encode the movement. An advantage of this embodiment is that it can reduce practitioner fatigue.

As mentioned above, the encoder maybe provided with sensory feedback for the practitioner. Various ways of providing such feedback are discussed in detail below.

C. The Control Circuit

The encoder 12 is coupled to the servo system 16 through the control circuit 14. The coupling of the encoder to the servo system may be wired or may be wireless. In a presently preferred embodiment, the encoder 12 is coupled by wires to the control circuit 14 and the output of the control circuit is coupled to the servo system 16 by wireless transmission. Those skilled in the art will appreciate that many different modes of coupling the encoder to the servo system are possible. It will also be appreciated that the type of control circuit utilized will depend in part on the type of encoder used and the type of servo system used.

1. Potentiometers to Servo Motors

For the encoder described above with reference to FIGS. 1 and 2, each potentiometer is coupled to two regulated reference voltages and provides a variable voltage output which is coupled to two timers which generate a pulse output for controlling a digital proportional servo motor.

Figure 12:
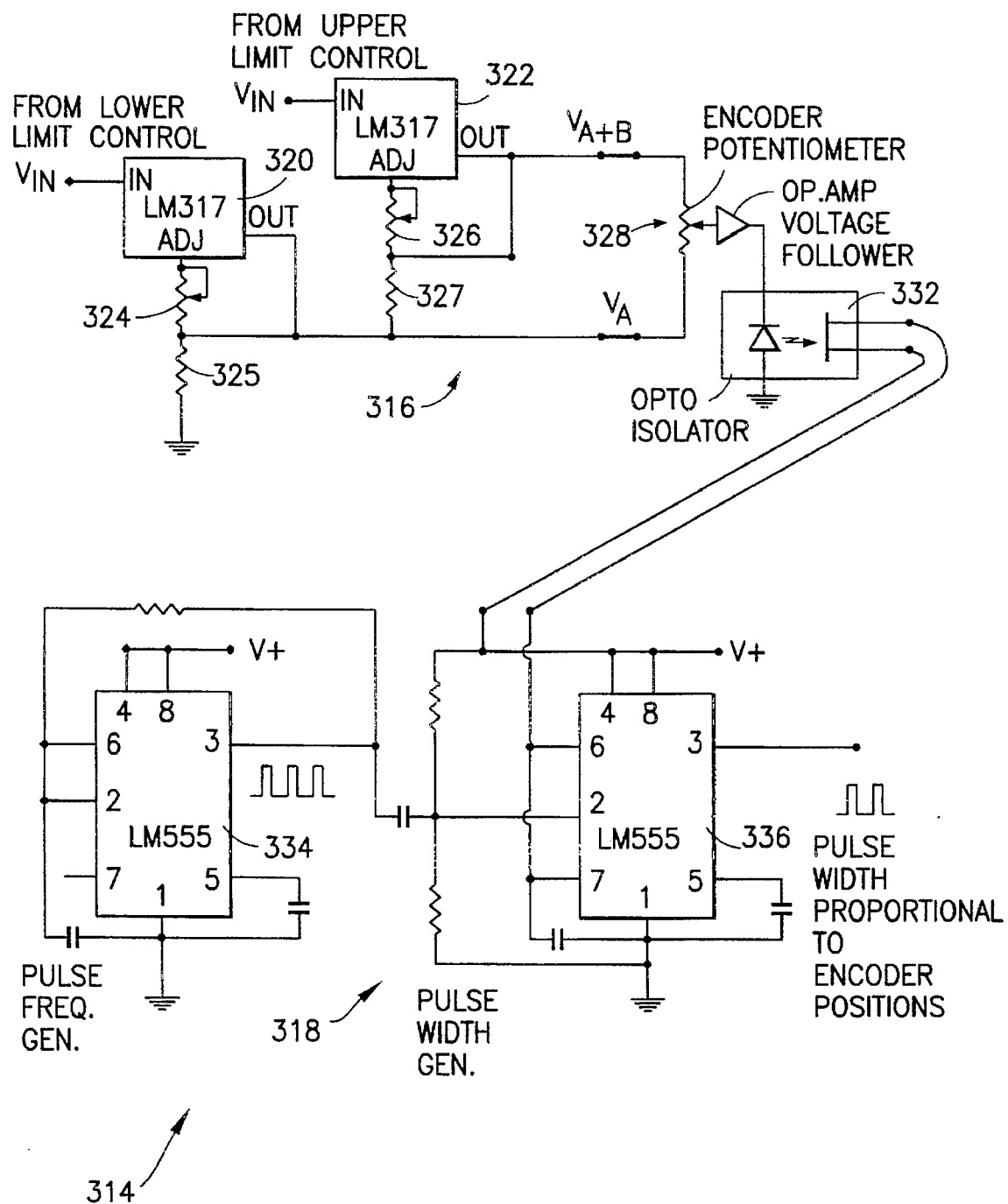
FIG. 12 is a schematic diagram of a control circuit of the encoder.

An exemplary control circuit is shown in FIG. 12 which represents one portion of the control circuit 314 for one potentiometer. It will be appreciated that for an encoder with fourteen potentiometers, the circuit of FIG. 12 will be replicated fourteen times. The exemplary circuit 314 has two parts: a reference voltage generator 316; and a pulse code generator 318. The reference voltage generator 316 includes two LM317 voltage regulators 320, 322 which are independently adjustable by variable resistors 324, 326 to produce a high reference voltgage $V_{A+B}$ and a low reference voltage $V_A$ from a single source voltage Vin. The potentiometer 328 from the encoder is connected to the high and low reference voltages and is provided with an op-amp voltage follower 330. The output of the voltage follower 330 is coupled to an opto-isolator 332. As the potentiometer 328 registers movement, a voltage between $V_{A+B}$ and $V_A$ is selected and fed through the opto-isolator 332 to produce an output voltage for the pulse code generator 318. The pulse code generator 318 includes two LM555 timers 334, 336, one for generating a pulse frequency and the other for generating a pulse width. The output from the opto-isolator 332 is coupled to the timer 336 which generates the pulse width, and a pulse output is produced where the width of the pulses is proportional to the encoder position as determined by the potentiometer 332.

According to the presently preferred embodiment, the first voltage regulator 320 is adjustable by a variable resistor 324 and provides an output $V_A$ which is also coupled to ground through a resistor 325. The second voltage regulator 322 is adjustable by a variable resistor 326 which is coupled to ground through the output $V_A$ of the first regulator and a second resistor 327. The second voltage regulator thereby produces and output $V_{A+B}$. The output of the first timer 334 is a pulse train having a particular frequency and the output of the second timer 336 is a pulse train having the particular frequency and a pulse width proportional to the encoder position.

The high and low reference voltages are selected for each servo motor individually depending on the range of movement which will be required for the particular motor. Thus, the reference voltages supplied to different potentiometers in the encoder will be different. Moreover, depending on the reference voltages supplied, the ranges of the potentiometers will be different as well.

2. Other Control Circuits

It will be appreciated that other control circuits may be used with the potentiometer encoder and that different encoders may require different control circuits.

D. The Servo System

The encoders and control circuits described above may be used with several different types of servo systems. These include servo motors with pulleys and tendons, direct drive servo motors, jack screws, hydraulics, and pneumatics, for example.

1. Servo Motors with Pulleys and Tendons

Turning now to FIGS. 13 through 23, the servo system 16 is seen to include a disposable aluminum or injection molded plastic pulley tray 402 and an upper and lower array of servo motors 404, 406. The pulley tray 402 contains fourteen pulleys 90, 92, 94, 96, 98, 100, 102, 104, 106, 108, 110, 112, 114, 116 supported by bearings (not shown). Seven pulleys 90, 92, 94, 96, 98, 100, 102 are engaged by the upper servo motor array 402 and seven pulleys 104, 106, 108, 110, 112, 114, 116 are engaged by the lower servo motor array 406. The pulleys sit in bushings and are sandwiched between the upper and lower servo motors.

Figure 13:
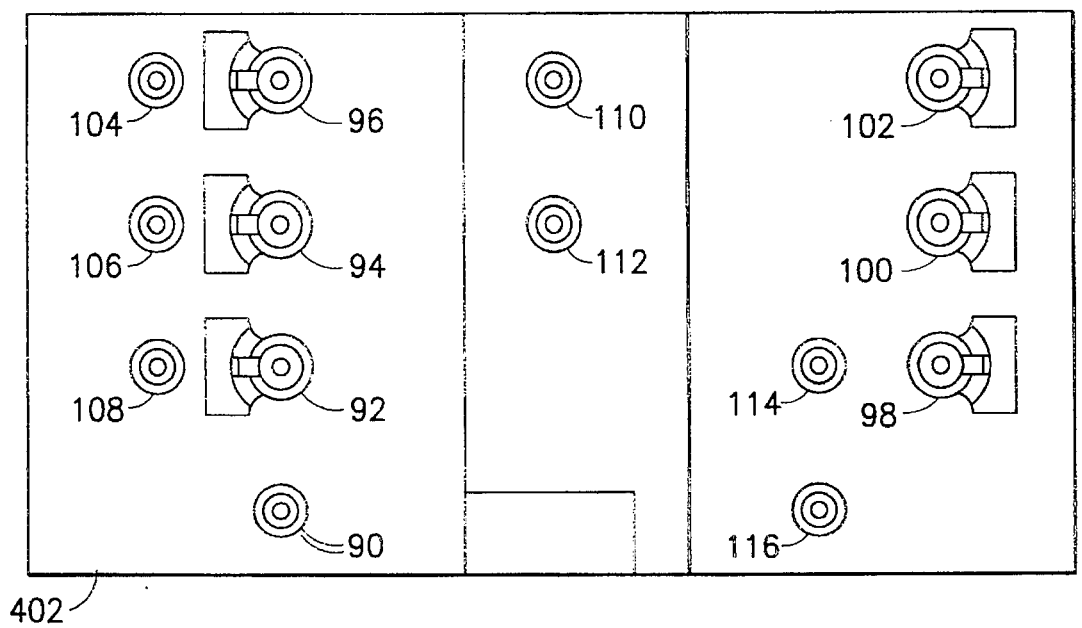
FIG. 13 is a top view of a pulley tray.
Figure 14:
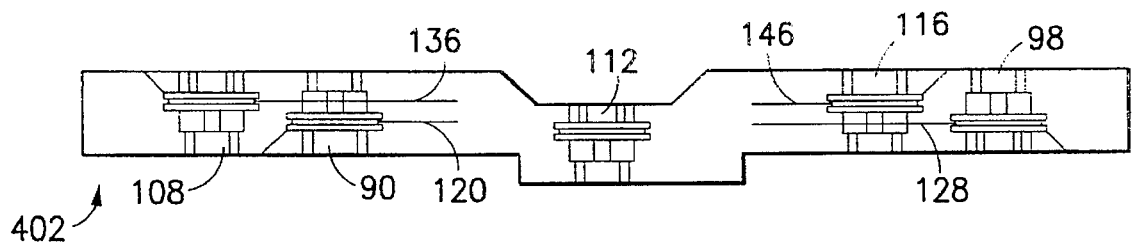
FIG. 14 is a transparent side elevation view of the pulley tray of FIG. 13.

As seen best in FIGS. 15 through 18, each pulley, e.g. 108, has a first cylindrical part 108a with a screw receiving bore 108b, a second cylindrical part 108c with a servo motor shaft receiving bore 108d and a pulley wheel 108e with a grooved rim 108f. The pulley wheel 108e is longitudinally offset from the center of the pulley, being closer to the first cylindrical part 108a and is provided with a radial slot 108g which extends from the groove 108f in the wheel rim to the screw receiving bore 108b. The screw receiving bore 108b has a stepped diameter, the larger part for receiving a screw head 109a and the smaller part being threaded. The pulleys are arranged in the pulley tray as shown in FIGS. 13 and 14 so that half of the pulleys have their shaft receiving bore (e.g. 108d) facing up and half have their shaft receiving bore facing down. The pulley tray has asymmetrical upper and lower surfaces so that the top and bottom of the tray are not confused. Tendons, e.g. 138, are attached to the pulleys, e.g. 108, by threading the ends of the tendon around the groove 108f in the pulley wheel, through the radial slot 108g and around the tendon locking screw 109 as seen best in FIGS. 17 and 18. The locking screw 109 is then tightened against the tendon 136.

Figure 23:
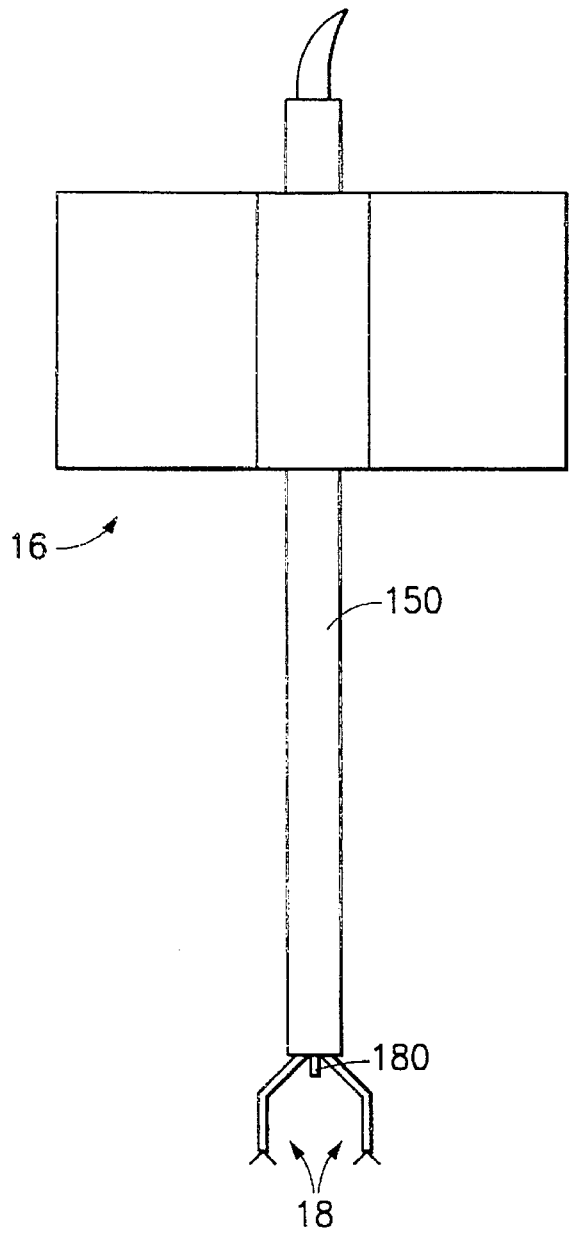
FIG. 23 is a plan view of an assembled servo motor tray, multilumen tube, and robot arms.

The tendons are threaded through the pulley tray as shown in FIG. 14 and exit the pulley tray through the multi-lumen tube 150 which is preferably rigidly attached to the pulley tray as shown in FIG. 23. It will be appreciated that the offset pulley wheels on oppositely mounted pulleys provide upper and lower space between tendons to ease the threading of the tendons through the tray and to thereby save space.

Figure 20:
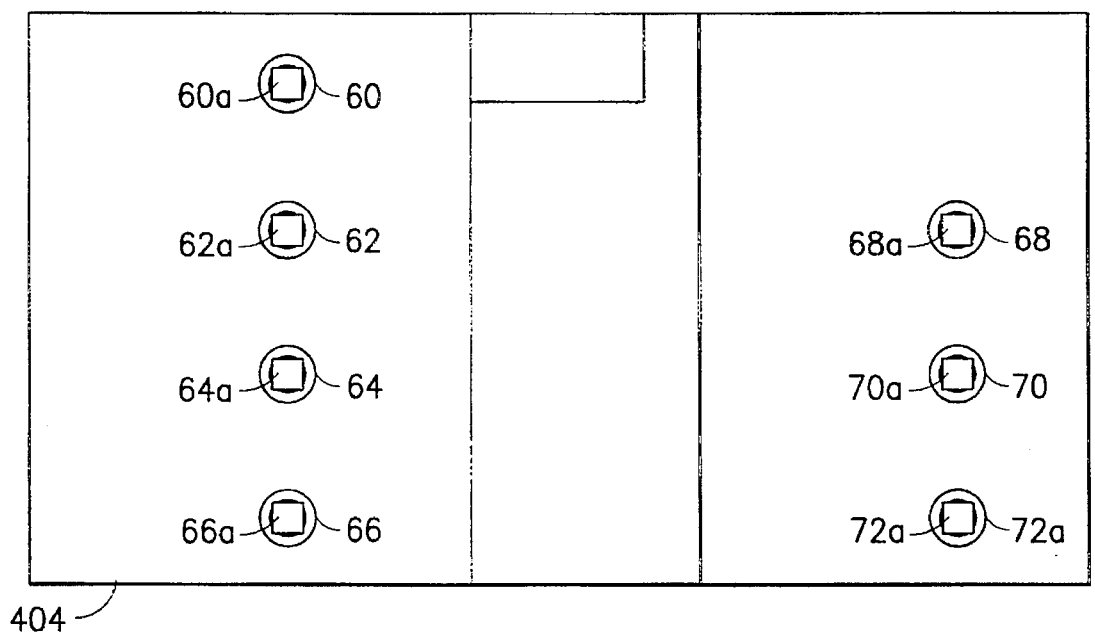
FIG. 20 is a bottom view of a top servo motor array.
Figure 21:
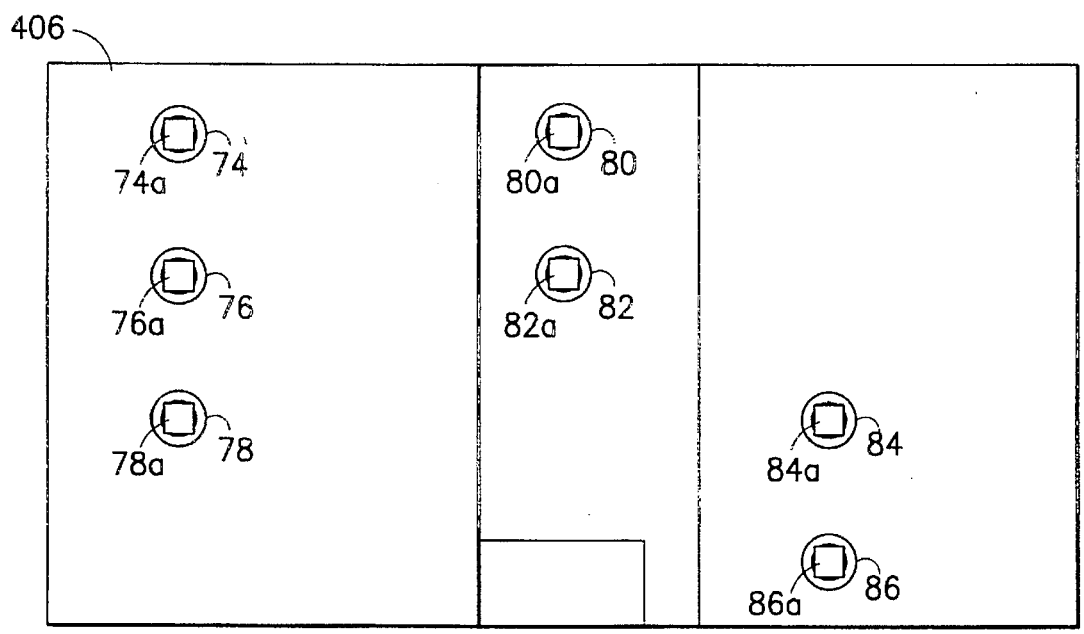
FIG. 21 is a top view of a bottom servo motor array.
Figure 22:
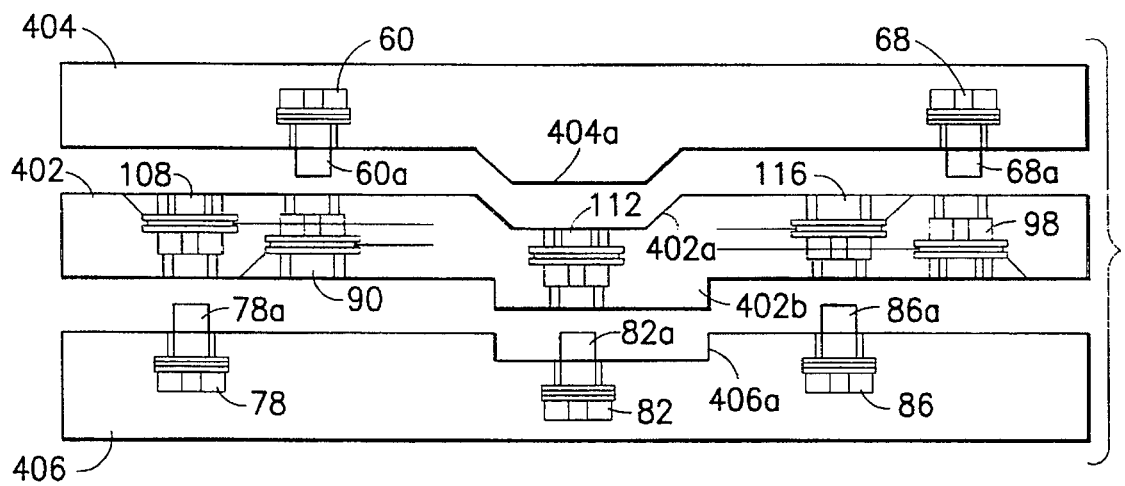
FIG. 22 is a transparent side elevation view of the top and bottom servo motor arrays and the pulley tray.

The pulley tray 402 is engaged by two servo motor arrays 404, 406. An upper servo motor array 404, which is shown in FIGS. 20 and 22, has seven servo motors 60, 62, 64, 66, 68, 70, 72 and a lower servo motor array 406, which is shown in FIGS. 21 and 22, has seven servo motors 74, 76, 78, 80, 82, 84, 86. Each servo motor has a splined shaft 60a, 62a, 64a, 66a, 68a, 70a, 72a, 74a, 76a, 78a, 80a, 82a, 84a, 86a which engages the shaft receiving bore, e.g. 108d, of a respective pulley. The splined shafts and the shaft receiving bores are "self-aligning". The servo system is assembled by placing the lower surface of the pulley tray on top of the upper surface of the lower servo motor array so that the splined shafts of the servo motors engage the shaft receiving bores of the pulleys. The lower surface of the upper servo motor array is then placed on top of the upper surface of the pulley tray so that the splined shafts of the servo motors engage the shaft receiving bores of the pulleys. The sandwiched assembly of servo motor arrays and pulley tray is then locked together to provide the assembly as shown in FIG. 23.

As seen best in FIG. 22, the upper surface of the pulley 402 tray is provided with a keyway 402a and the lower surface of the upper servo motor array 404 is provided with a key 404a which engages the keyway 402a. Similarly, the upper surface of the lower servo motor array 406 is provided with a keyway 406a and the lower surface of the pulley tray 402 is provided with a key 402b which engages the keyway 406a. Thus, it is impossible to couple the servo motor arrays to the pulley tray incorrectly.

As mentioned above, the described servo system permits a portion of the robotic tool to be reusable while another portion may be disposable, if desired. In particular, the encoder, the control circuit, and the servo motors are reusable. The pulleys, tendons, multi-lumen tube and robot arms which will be in contact with human fluids, may be uncoupled from the servo motors and disposed of, if desired. In addition, the described servo system permits the use of several different types of robot arms with the same encoder. For example, one type of robot arms may have two grippers whereas another type of robot arms may have a gripper and a cutter, etc. The self-aligning feature of the servo system permits rapid coupling and uncoupling of the servo motors and the pulleys so that different types of robot arms can be used with the same encoder during a single endoscopic procedure.

2. Direct Drive and Pullwire

According to a presently preferred embodiment, the shoulder rotation joint 160 (FIG. 1) of each robot arm (which is described in detail below) is coupled to a respective servo motor by a direct drive instead of by a pulley and tendon. This simplifies operation and a direct connection is better for these joints which have the highest loads. In addition, while the tendons described above are "endless loops", the tendon which controls the gripper 172 is preferably a single pull wire which is described in detail in the following discussion of the robot arms.

As indicated previously herein, the use of pulleys in the servo assembly may require positional feedback from the robot arms (discussed in detail below) to compensate for slippage and stretch and requires the careful alignment of the servo motors with the pulleys (using the self-aligning splined shafts discussed above). The need for positional feedback and careful alignment of the servo motors may be avoided through the use of jack screws in place of pulleys.

3. Jack Screws In Lieu of Pulleys

Figure 24:
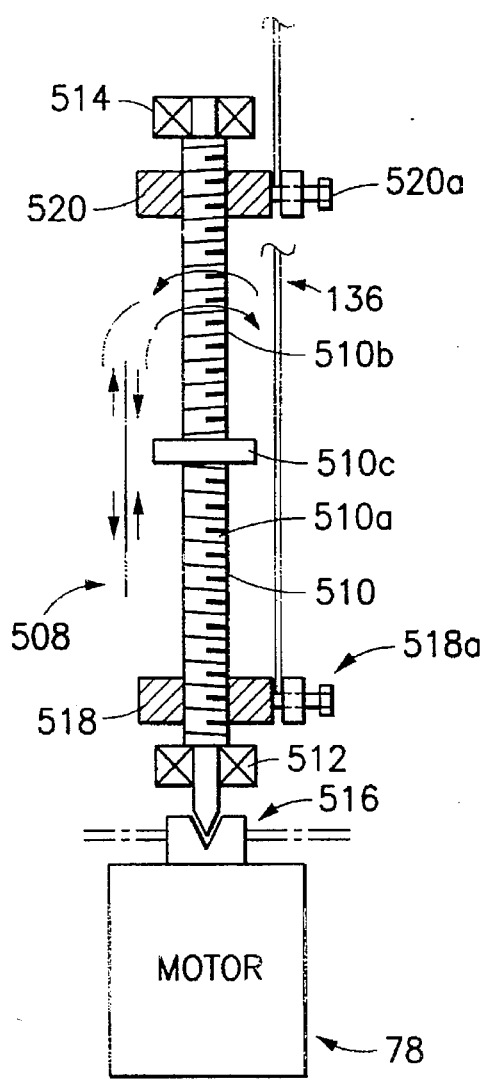
FIG. 24 is a schematic plan view of a jack screw coupled to a servo motor and a tendon loop.

As shown in FIG. 24, a jack screw 508 has a rotational shaft 510 mounted for rotation on two bearings 512, 514. One end of the shaft has a self-aligning coupling 516 for removable coupling with a Servo motor 78. Half for the shaft 510a is left hand threaded and the other half 510b of the shaft is right hand threaded. Each half of the shaft has a screw jack nut 518, 520 threaded to it and an indexing track (not shown) engages the nuts 518, 520 to prevent them from rotating when the shaft 510 is rotated. Each screw jack nut has a tendon coupling clamp 518a, 520a and the two ends of a tendon loop 136 are coupled to respective screw jack nuts by means of the tendon coupling claps. When the shaft is rotated in one direction, the screw jack nuts are driven towards the center 510 of the shaft. Conversely, when the shaft is rotated in the other direction, the screw jack nuts are driven outward from the center 510c of the shaft to the ends of the shaft. The use of screw jacks may obviate the need for positional feedback since the input signal is in 1:1 proportion with the position; however, it may still be desirable to use positional feedback from the actual end effector to compensate for slack or stretch in the connecting tendons or linkages.

With jack screws, the interface with the servo motors is less critical than with pulleys. This is because several rotations of the servo motor are required to effect an appreciable joint movement, depending on the screw pitch.

E. The Robot Arms

1. Socket and Clevis Arrangement

Figure 25:
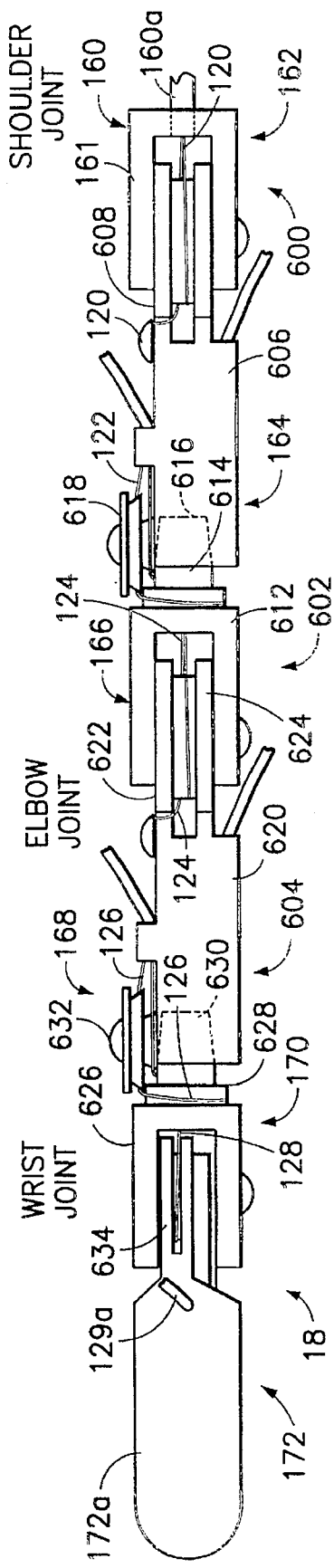
FIG. 25 is a broken side elevation view of a robot arm according to the invention.
Figure 26:
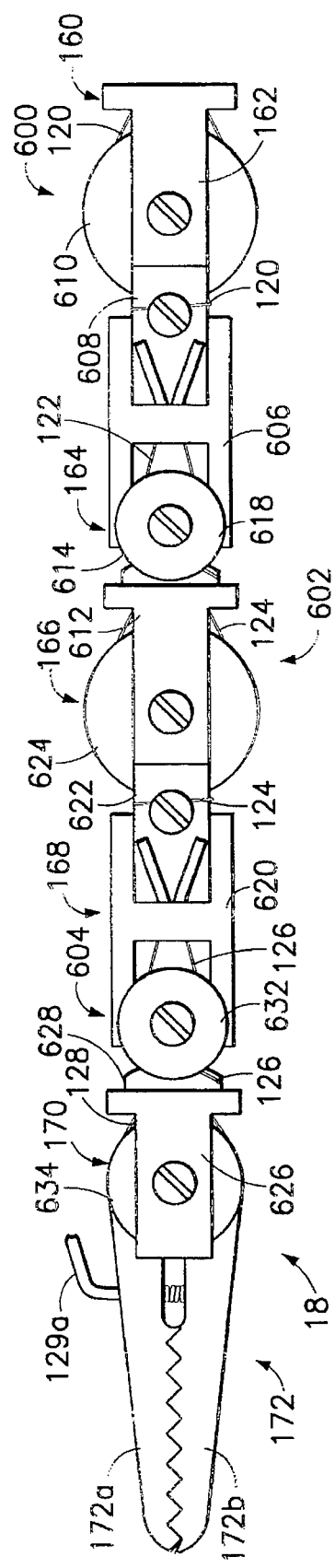
FIG. 26 is a view similar to FIG. 25, but rotated 90° about the shoulder axis.
Figure 27:
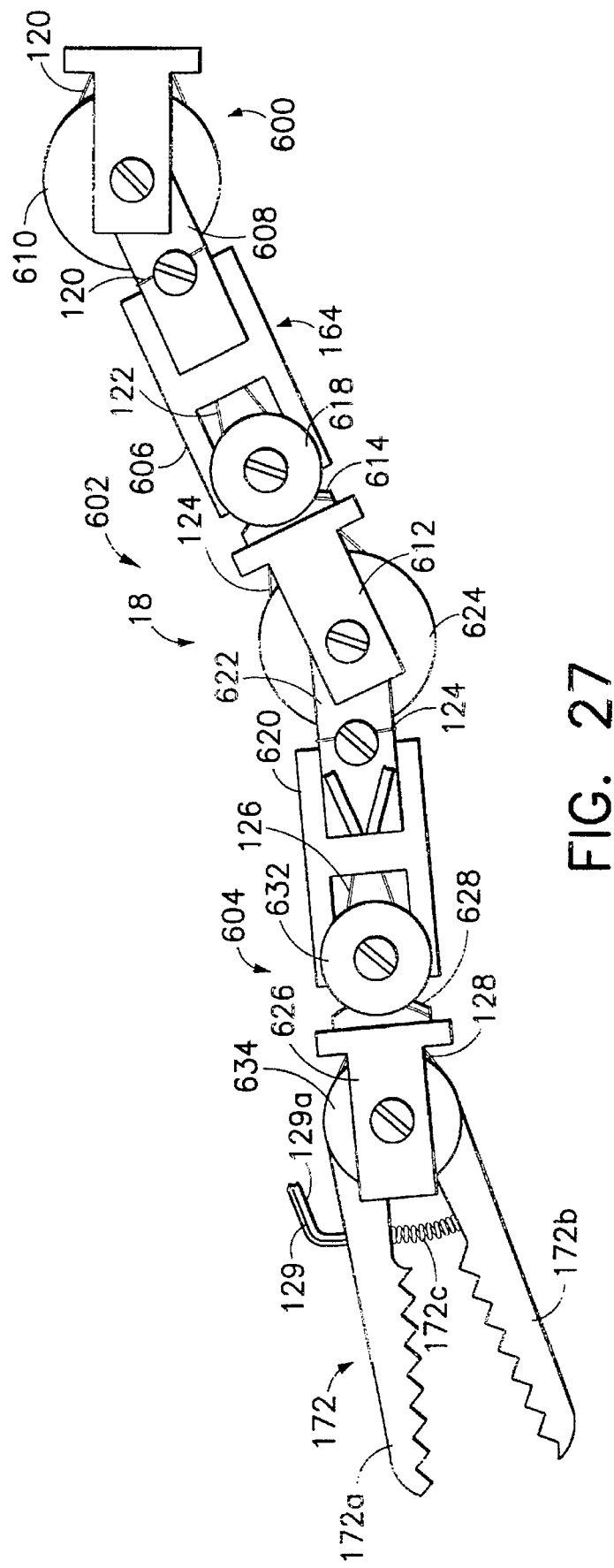
FIG. 27 is a view similar to FIG. 26 with two flexional joints flexed and grippers opened.
Figure 28:
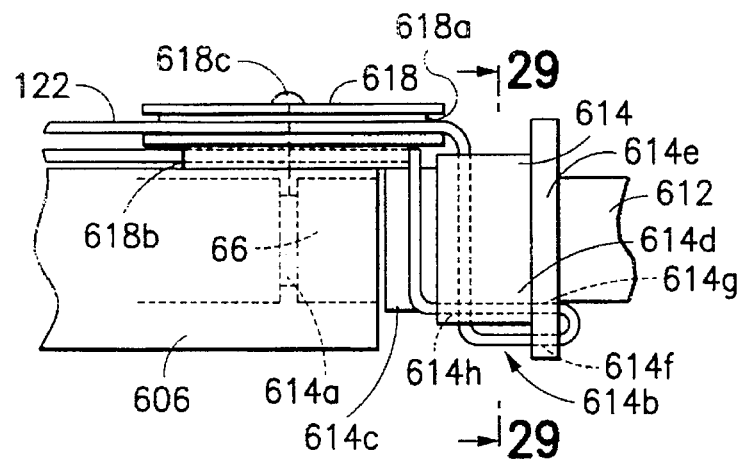
FIG. 28 is a broken side elevation view of a portion of a robotic rotation joint of FIGS. 25-27.
Figure 29:
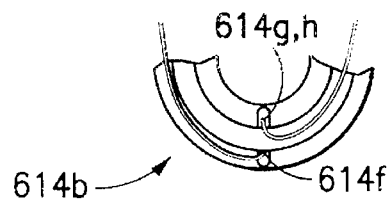
FIG. 29 is a broken cross sectional view along line 29—29 in FIG. 28.
Figure 30:
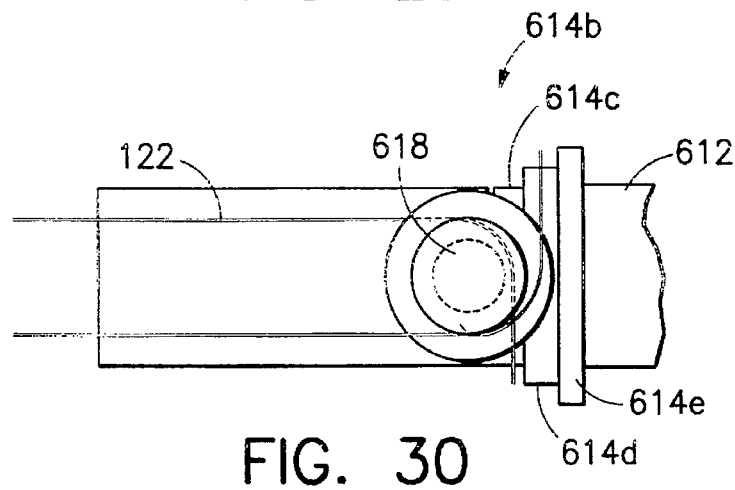
FIG. 30 is a broken top view of the robotic rotation joint of FIGS. 28 and 29.
Figure 31:
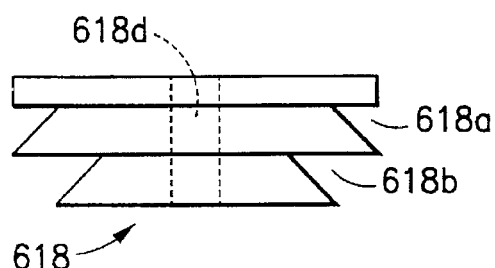
FIG. 31 is an enlarged side elevation of a rotation pulley.

FIGS. 25 through 27 show a presently preferred embodiment of one of the two robot arms 18. The robot arms approximate the geometry of the encoder which approximates the geometry of the arms of the practitioner. Each robot arm generally includes a shoulder 600, an elbow 602, a wrist 604, and a pair of grippers 172 (172a, 172b). The shoulder 600, elbow 602 and wrist 604 each have a rotational joint 160, 164, 168 and a flexional joint 162, 166, 170. The axis of rotation of each rotational joint is always perpendicular to the axis of flexion of the corresponding flexional joint, regardless of their rotational or flexional position. There are, therefore, three rotational joints and three flexional joints. The presently preferred joints are configured as alternating socket and clevis members. A clevis is mounted for rotation in a socket and a socket is mounted for flexion in a clevis. A presently preferred embodiment of this joint configuration is described as follows.

With reference to FIGS. 25–27, the first joint in the robot arm is the shoulder rotational joint 160 which is proximally coupled to a direct drive torque tube (not shown) and has a distal shoulder clevis 161. The shoulder rotational joint 160 has a cylindrical bore 160a which extends into the shoulder clevis 161.

The second joint is the shoulder flexional joint 162 which is formed by mounting an elbow socket 606 in the shoulder clevis 161. The elbow socket 606 has a stem 608 which is mounted between the arms of the shoulder clevis 161. A shoulder flexion pulley 610 is mounted on the elbow socket stem 608 between the arms of the shoulder clevis 161 and is rotatable about an axis which is perpendicular to the axis of the shoulder rotation. A shoulder flexion tendon 120 is wrapped around the shoulder flexion pulley 610 and around the stem 608 of the elbow socket 606 as described in more detail below. The tendon 120 extends proximally through the bore 160a in the shoulder rotational joint 160 back to the pulley tray described above.

The third joint is the elbow rotational joint 164 which is formed by the elbow socket 606 and an elbow clevis 612 having a stem 614 which is rotationally mounted in the cylindrical bore 616 of the elbow socket 606. An elbow rotation pulley 618 is mounted on the elbow socket 606 and is rotatable about an axis perpendicular to the axis of rotation of the elbow clevis 612. An elbow rotation tendon 122 is wrapped around the elbow rotation pulley 618 and around the elbow clevis stem 614 as described in more detail below.

The fourth joint is the elbow flexional joint 166 which is formed by mounting a wrist socket 620 in the elbow clevis 612. The wrist socket 620 is similar to the elbow socket 606 and has a stem 622 which is mounted between the arms of the elbow clevis 612. An elbow flexion pulley 624 is mounted on the wrist socket stem 622 between the arms of the elbow clevis 612 and is rotatable about an axis which is perpendicular to the axis of the elbow rotation. An elbow flexion tendon 124 is wrapped around the elbow flexion pulley 624 and around the stem 622 of the wrist socket 620 as described in more detail below.

The fifth joint is the wrist rotational joint 168 which is formed by the wrist socket 620 and a wrist clevis 626 having a stem 628 which is rotationally mounted in the cylindrical bore 630 of the wrist socket 620. A wrist rotation pulley 632 is mounted on the wrist socket 620 and is rotatable about an axis perpendicular to the axis of rotation of the wrist clevis 626. A wrist rotation tendon 126 is wrapped around the wrist rotation pulley 632 and around the wrist clevis stem 628 as described in more detail below.

The sixth joint is the wrist flexional joint which is formed by mounting a pair of grippers 172 between the arms of the wrist clevis 626. A wrist flexion pulley 634 is mounted on one of the grippers, e.g. 172a, between the arms of the wrist clevis 626 and is rotatable about an axis which is perpendicular to the axis of the wrist rotation. A wrist flexion tendon 128 is wrapped around the wrist flexion pulley 634 as described in more detail below.

The grippers 172a, 172b are biased to the open position as shown in FIG. 27 by a coil spring 172c. Each gripper is provided with a bore for receiving a gripper tendon 129 which is axially movable in a tendon sheath 129a. The gripper tendon 129 passes freely through the bore in the first gripper 172a and the coil spring 172c and is fixed inside the bore of the second gripper 172b. The tendon sheath 129a abuts the outer surface of first gripper 172a. When the gripper tendon 129 is pulled axially through the tendon sheath 129a in a proximal direction, the distal end of the gripper tendon and the distal end of the tendon sheath move the grippers together against the force of the spring to the closed position shown in FIG. 26. When the gripper tendon is released, the spring returns the grippers to the open position shown in FIG. 27. The first gripper 172a is analogous to the palm of the surgeon's hand and the second gripper 172b is analogous to an articulating thumb.

The robot arms 18 have an overall thickness of approximately 6.25 mm and the relative size of each of the joints is proportional to the size of corresponding parts of a human arm. The tendons are preferably thin multistranded wires. The proximal joints may use stronger wires than the distal joints. The flexion joints may use thicker wires than the rotation joints. Each tendon preferably has its own sheath except for the shoulder flexion tendon 120 which has a straight run from the pulley tray to the shoulder flexion joint. All of the tendons other than the shoulder flexion tendon are preferably carried in lumen of the multi-lumen tube and enter to the pulleys on the robot arm though bores in the respective joints.

2. Rotational and Flexional Pulleys and Tendons

FIGS. 28 through 31 show details of the presently preferred embodiment of the elbow and wrist rotational joints. As seen best in FIG. 28 and 31, the rotation pulley 618 has two layers, with an upper tendon groove 618a and a lower tendon groove 618b, and is mounted tangentially to the socket 606 with a screw 618c which passes through a bore 618d in the pulley 618. The pulley preferably has an overall diameter of approximately 0.180". The grooves 618a, 618b are approximately 0.015" wide, and the diameter of the bottom portion of the pulley is approximately 0.140".

The stem 614 of the clevis 612 has a circumferential mounting groove 614a which is used to hold the stem in the socket 606 and the end of the screw 618c may engage the groove 614a for this purpose. A twist drum 614b is provided on a portion of the stem external of and immediately adjacent to the socket 606. The twist drum is formed by two collars 614c, 614d and a flange 614e of increasing outer diameter. The diameter of the first collar 614c is preferably approximately 0.170" and it extends for a length of approximately 0.030". The diameter of the second collar 614d is preferably approximately 0.20" and it extends for a length of approximately 0.040". The diameter of the flange 614e is preferably approximately 0.250". The flange 614e has a first longitudinal bore 614f and a second longitudinal bore 614g which are spaced apart from each other radially as seen best in FIGS. 28 and 29. The second collar 614d has a longitudinal bore 614h which is radially aligned with the second bore 614g in the flange 614e. These bores form a path for the rotation tendon as described below.

The rotation tendon 122 loops approximately 90° around the lower tendon groove 618b of the pulley 618, turns at a substantially right angle, and loops approximately 180° around the first collar 614c of the twist drum 614b. The tendon then passes into the bore 614h of the second collar and through the bore 614g of the flange. The tendon bends approximately 180° and passes through the bore 614f in the flange and loops approximately 180° around the second collar 614d of the twist drum in a direction opposite to the loop around the first collar of the twist drum. The tendon exits the twist drum with a substantially right angle turn and loops approximately 90° around the upper tendon groove 618a of the pulley. The layers of the pulley and the increasing diameters of the twist drum prevent the tendon 122 from crossing over itself and suffering premature wear from frictional contact. The bores in the twist drum anchor the tendon so that it does not slip off the second collar onto the first collar.

From the foregoing and the description of the servo system above, those skilled in the art will appreciate that rotation of the tendon loop 122 at the servo system end results in rotation of the clevis in the robot arm. This design allows a rotation of the rotational joints up to about 270°.

Figure 32:
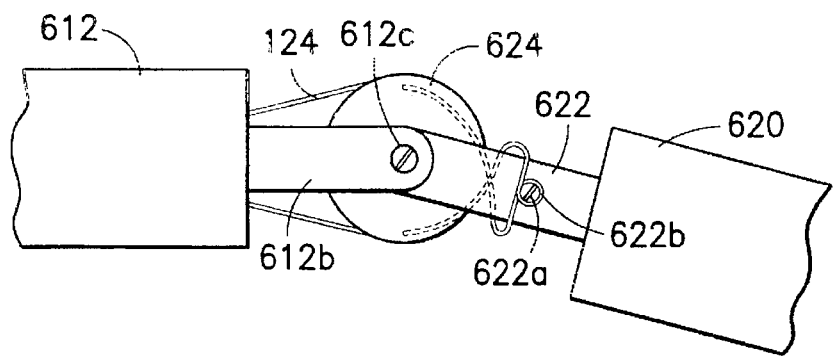
FIG. 32 is a broken side elevation view of a robotic flexion joint according to the invention.
Figure 33:
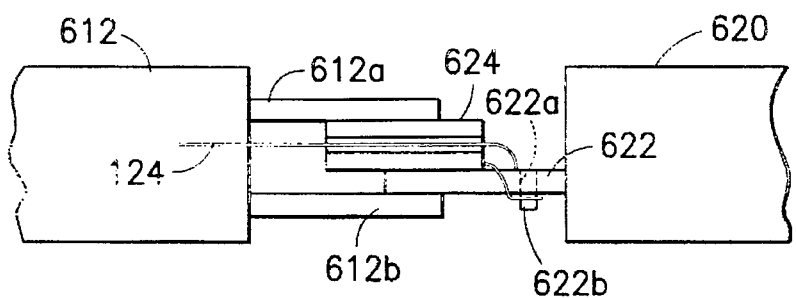
FIG. 33 is a top view of the robotic flexion joint of FIG. 32.

FIGS. 32 and 33 show details of the presently preferred embodiment of the shoulder, elbow and wrist flexional joints. The clevis arms 612a, 612b are provided with a clevis pin 612c (screw) upon which the stem 622 of a corresponding socket 620 is rotationally mounted. A flexion pulley 624 is also mounted between the clevis arms 612a, 612b and is coupled to the socket stem 622. The socket stem 622 is provided with a threaded hole 622a having a tendon locking screw 622b which is located between the flexion pulley 624 and the socket 620. The flexion tendon 124 wraps approximately 90° around one side of the flexion pulley 624, approximately half way around the socket stem 622, is looped around the tendon locking screw 622b, wraps around the other half of the socket stem 622 and wraps approximately 90° around the other side of the flexion pulley 624.

3. Path of Tendons, Direct Drive Shoulder, Pullwire for Grippers

Figure 34:
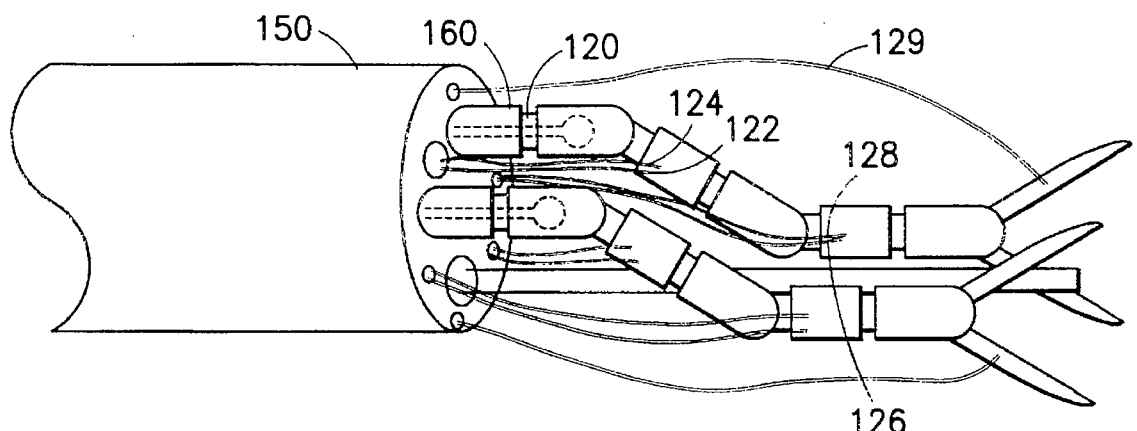
FIG. 34 is a broken perspective view of two robotic arms extending from the distal end of a multi-lumen tube.

As mentioned above, each of the tendons 122–129 is protected by its own sheath and extends through a lumen in the multilumen tube 150 as shown in FIG. 34. The shoulder flexion tendon 120 is preferably delivered to the shoulder flexion joint directly through the torque tube 160 which forms the shoulder rotation joint. It will also be appreciated that when the grippers are activated by a pullwire arrangement, the tendon 129 will not be a tendon loop like the other tendons.

4. Other End Effectors

While the robotic arms described above have been shown with gripper end effectors, it will be appreciated that the arms could be provided with any type of end effector such as a cutter, dissector, bioptome, etc. Moreover, it will be further appreciated that the end effectors could easily be provided with cautery capability, either monopolar or bipolar. In addition, either the end effectors or the multilumen tube could be provided with suction and/or irrigation capabilities.

5. Interchangeable End Effectors

As mentioned above, the end effectors may be interchanged during the course of a procedure by detaching the pulley 22, tray/multilumen tube/robot arms assembly from the servo motor arrays. In addition, however, it is possible to provide interchangeable end effectors at the distal ends of the robot arms so that the robot arms may be configured for a particular procedure. For example, since the gripper is controlled by a single tendon pull-wire, the gripper can be removably coupled to the wrist joint and the pull-wire can be removably coupled to the gripper.

F. Feedback Means

1. Visual Feedback to the Practitioner a. Fiber Optics and Video Camera

As mentioned in the overview section above, one embodiment of the endoscopic robotic tool includes a lens at the distal end of the multi-lumen tube 150 (FIG. 1) which is optically coupled to a television camera. Typically, the lens is a "fish eye" or other type of wide angle lens 180 and the optical coupling is through fiber optics or a rigid relay-lens system. A relay lens system is optically coupled to the lens and extends through the tube to the proximal end of the tube where it is optically coupled to a CCD video detector or similar device. A fiber optic bundle is optically coupled to a light source and extends through to the distal end of the tube below the fish eye lens. The image formed on the CCD is processed by a video circuit and transmitted to a video display 182 for viewing by the practitioner. Preferably, an additional video display is provided for the practitioner's assistant.

b. Stereoscopic

The basic video feedback described above can be enhanced in several ways. For example, the video circuit may be provided with means for horizontally transposing the image so that the sensory effect of viewing the surgical site is like looking in a mirror. Some practitioners may find this transposed view easier to coordinate robot arm movements. Moreover, a stereoscopic visual feedback can be provided using a second lens, relay lens and CCD arrangement or by processing the image formed by one lens. For example, given a sufficiently high resolution CCD, different portions of the image formed on the CCD may be selected and displayed on separate video displays, one left and the other right, to simulate a stereoscopic view of the surgical site. In addition, the stereoscopic view may be further enhanced by using "goggle type" video displays which place a small high resolution video display directly in front of each of the practitioner's eyes. This also allows the practitioner to assume a comfortable head position during the procedure and reduces fatigue during a lengthy procedure.

c. Non-Visible Spectrum

It will also be appreciated that the visual feedback need not be based on visual information or on information which is visible to the human eye. The video display may include numeric data relating to the patient's vital signs, coordinates indicating the location of the robot arms inside the patient's body, and other data. These data may be displayed alphanumerically or graphically. The visual information from the endoscopic lens may include that seen in visible light, infrared, and ultraviolet through the use of a broad band CCD and electronic video filters. In addition, a radiography or sonography equipment may be placed over the surgical site to provide a visual "road map" of the patient's body. The radiogram or sonogram may be superimposed over the visual image supplied by the endoscopic lens. The contents and format of the video display may be preconfigured by the practitioner according to individual preference by setting the video circuit through a keyboard for example. Selection among different display contents and/or formats during the course of a procedure can be "toggled" by a foot switch or by a switch on the pistol grip of the encoder.

2. Servo Position Feedback

It may be necessary or desirable to provide positional feedback for the servo motor system. Those skilled in the art will appreciate that each joint described above may be provided with a position transducer which provides feedback to the control circuit so that the robot arms are indeed moved to the desired position by the servo motors, tendons, and pulleys.

3. Encoder Sensory Feedback

As mentioned above, it may also be advantageous to provide sensory feedback to the practitioner via the encoder unit. The most useful type of feedback is the force feedback to the trigger as described above. However, other feedback such as temperature feedback and tensile feedback may also be useful.

G. The Multi-lumen Tube

FIGS. 1, 23 and 34 show the distal end of the multi-lumen tube 150 with the two robot arms 18 extending therefrom. One of the lumens of the multi-lumen tube is provided for an endoscope 180. At least one other lumen is provided for the delivery of supplies such as needles, sutures, hemostats, etc., for use by the robot arms. Other lumen may be provided for irrigation and/or suction, and for illumination.

The multi-lumen tube is preferably rigid, approximately 15 mm in diameter and is preferably covered with a TEFLON sheath along substantially its entire length. However, those skilled in the art will appreciate that the multilumen tube could be made flexible with some minor adjustments to the system described.

H. Remote Communications

As mentioned above, the robotic tools described herein may be utilized in a manner in which the practitioner is located a relatively great distance from the patient. Since the encoder and the feedback system are electronically linked to the servo system, endoscope, etc., there is virtually no limit to the distance which may separate the practitioner from the patient. Thus, in an emergency situation, an expert practitioner can be made available to a patient who is many miles away. Also, where a patient is located in dangerous surroundings, such as a battle field, a practitioner need not be exposed to the same hazards in order to effect a procedure utilizing the tools described herein. Moreover, in cases of extremely contagious disease, the tools described herein allow the practitioner to be safely isolated from the patient. Those skilled in the art of telecommunications will appreciate how easily the communications link between the practitioner and the robotic tools can be established.

There have been described and illustrated herein several embodiments of endoscopic robotic surgical tools and methods. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as so claimed.

We claim:

1. An endoscopic surgical instrument for use by a medical practitioner to perform an endoscopic procedure at a surgical site within a body of a patient, said instrument comprising:

a) encoder means for encoding movements of a first arm of the practitioner;

b) controller means coupled to said encoder means for translating the movements of the first arm of the practitioner into a transmissible signal;

c) drive means coupled to said controller means for generating mechanical energy in response to said transmissible signal; and d) a first robotic arm having a plurality of joints, locatable within the body, and having a first end effector, wherein said drive means is coupled to said first robotic arm for transmitting mechanical energy to said first robotic arm to follow at least some of the movements of the first arm of the practitioner.

2. An endoscopic surgical instrument according to claim 1, further comprising:

e) visual feedback means for providing a visual image of the surgical site to the practitioner.

3. An endoscopic surgical instrument according to claim 1, further comprising:

e) a second robotic arm having a plurality of joints, locatable within the body, and having a second end effector, wherein
said encoder means encodes movements a second arm of the practitioner, said controller means translates the movements of the second arm of the practitioner into a transmissible signal, and said drive means is coupled to said second robotic arm for transmitting mechanical energy to said second robotic arm to follow at least some of the movements of the second arm of the practitioner.

4. An endoscopic surgical instrument according to claim 1, wherein:

said first robotic arm has at least two rotational joints and at least two flexional joints.

5. An endoscopic surgical instrument according to claim 3, wherein:

said first and second robotic arms each have at least two rotational joints and at least two flexional joints.

6. An endoscopic surgical instrument according to claim 1, wherein:

said first robotic arm includes at least four of i) a shoulder rotational joint which replicates shoulder rotation of a respective arm of the practitioner;

ii) a shoulder flexional joint which replicates shoulder flexion of a respective arm of the practitioner;

iii) an upper arm rotational joint which replicates upper arm rotation of a respective arm of the practitioner;

iv) an elbow flexional joint which replicates elbow flexion of a respective arm of the practitioner;

v) a wrist rotational joint which replicates wrist rotation of a respective arm of the practitioner; and vi) a wrist flexional joint which replicates wrist flexion of a respective arm of the practitioner.

7. An endoscopic surgical instrument according to claim 3, wherein:

said first and second robotic arms each includes at least four of i) a shoulder rotational joint which replicates shoulder rotation of a respective arm of the practitioner;

ii) a shoulder flexional joint which replicates shoulder flexion of a respective arm of the practitioner;

iii) an upper arm rotational joint which replicates upper arm rotation of a respective arm of the practitioner;

iv) an elbow flexional joint which replicates elbow flexion of a respective arm of the practitioner;

v) a wrist rotational joint which replicates wrist rotation of a respective arm of the practitioner; and vi) a wrist flexional joint which replicates wrist flexion of a respective arm of the practitioner.

8. An endoscopic surgical instrument according to claim 1, wherein:

said first end effector is a gripper, said encoder means includes a first pistol grip, and said gripper closes in response to said pistol grip.

9. An endoscopic surgical instrument according to claim 3, wherein:

said first and second end effectors are grippers, said encoder means includes first and second pistol grips, and said grippers close in response to said pistol grips.

10. An endoscopic surgical instrument according to claim 1, wherein:

said encoder means comprises an exoskeleton having a plurality of joints, and a plurality of transducers coupled to said joints for encoding relative movement of said joints, said exoskeleton being attachable to the first arm of the practitioner so that movement of the first arm of the practitioner is tracked by said exoskeleton and encoded by said transducers.

11. An endoscopic surgical instrument according to claim 3, wherein:

said encoder means comprises an exoskeleton having a plurality of joints, and a plurality of transducers coupled to said joints for encoding relative movement of said joints, said exoskeleton being attachable to the first and second arm of the practitioner so that movement of the first and second arms of the practitioner is tracked by said exoskeleton and encoded by said transducers.

12. An endoscopic surgical instrument according to claim 10, wherein:

said transducers include potentiometers and said drive means include servo motors.

13. An endoscopic surgical instrument according to claim 12, wherein:

at least some of said drive means are coupled to said first robotic arm by flexible tendons.

14. An endoscopic surgical instrument according to claim 11, wherein:

said transducers include potentiometers and said drive means include servo motors.

15. An endoscopic surgical instrument according to claim 14, wherein: at least some of said drive means are coupled to said first and second robotic arms by flexible tendons.

* * * * *

UNITED STATES PATENT AND TRADEMARK OFFICE
CERTIFICATE OF CORRECTION

PATENT NO. : 5,624,398
DATED : April 29, 1997
INVENTOR(S) : Kevin W. SMITH et al.

It is certified that error appears in the above-indentified patent and that said Letters Patent is hereby corrected as shown below:

On the Title Page, Item "[56] References Cited" under U.S. PATENT DOCUMENTS, please add:

| | | |
|---|---|---|
| 5,251,611 | 10/1993 | Zehel et al |
| 5,313,306 | 5/1994 | Kuban et al. |
| 5,337,732 | 8/1994 | Grundfest et al. |
| 5,368,015 | 11/1994 | Wilk |
| 5,417,210 | 5/1995 | Funda et al. |
| 5,528,955 | 6/1996 | Hannaford et al.. |
| 5,545,120 | 8/1996 | Chen et al. |
| 5,553,198 | 9/1996 | Wang et al. |
| 5,556,370 | 9/1996 | Maynard |

Signed and Sealed this

Twenty-third Day of February, 1999

Attest:

Q. TODD DICKINSON

*Attesting Officer*     *Acting Commissioner of Patents and Trademarks*